United States Patent
Reynolds et al.

(10) Patent No.: US 9,034,355 B2
(45) Date of Patent: May 19, 2015

(54) MATERIALS FOR MODULATING BIOLOGICAL RESPONSES AND METHODS OF MAKING

(75) Inventors: Melissa M. Reynolds, Fort Collins, CO (US); Vinod B. Damodaran, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 471 days.

(21) Appl. No.: 13/403,557

(22) Filed: Feb. 23, 2012

(65) Prior Publication Data

US 2015/0004257 A1    Jan. 1, 2015

Related U.S. Application Data

(60) Provisional application No. 61/446,121, filed on Feb. 24, 2011.

(51) Int. Cl.
| | | |
|---|---|---|
| *A61K 47/30* | (2006.01) | |
| *A61K 9/70* | (2006.01) | |
| *A61K 47/48* | (2006.01) | |
| *A61K 33/00* | (2006.01) | |

(52) U.S. Cl.
CPC ........... *A61K 47/4823* (2013.01); *A61K 47/482* (2013.01); *A61K 33/00* (2013.01)

(58) Field of Classification Search
CPC ..... A61K 9/70; A61K 47/30; A61L 2300/114
USPC ............... 424/422, 423, 718, 443; 514/772.3, 514/788, 645
See application file for complete search history.

(56) References Cited

U.S. PATENT DOCUMENTS

| | | | |
|---|---|---|---|
| 5,691,423 A | 11/1997 | Smith et al. | |
| 6,451,337 B1 | 9/2002 | Smith et al. | |
| 7,087,709 B2 | 8/2006 | Stamler et al. | |
| 7,425,218 B2 | 9/2008 | Keefer et al. | |
| 7,829,553 B2 | 11/2010 | Arnold et al. | |
| 8,771,756 B2 | 7/2014 | Reynolds et al. | |
| 2004/0087510 A1 | 5/2004 | Garvey et al. | |
| 2005/0220756 A1 | 10/2005 | Stamler et al. | |
| 2005/0265958 A1 | 12/2005 | West et al. | |
| 2006/0153795 A1 | 7/2006 | West et al. | |
| 2008/0220048 A1 | 9/2008 | Chen et al. | |
| 2008/0255101 A1 | 10/2008 | Garvey et al. | |
| 2008/0306012 A1 | 12/2008 | Hrabie et al. | |
| 2011/0159116 A1 | 6/2011 | Reynolds et al. | |
| 2014/0178504 A1 | 6/2014 | Reynolds et al. | |

OTHER PUBLICATIONS

International Search Report and Written Opinion issued in PCT/US2012/026317, mailed Jun. 6, 2012, 10 pages.

Damodaran, Vinod Babu et al., "Conformational Studies of Covalently Grafted Poly(ethylene Glycol) on Modified Solid Matrices Using X-ray Photoelectron Spectroscopy", Langmuir 2010, vol. 26, No. 10, pp. 7299-7306.

Ellman, George L. "Tissue Sulfhydryl Groups", Archives of Biochemistry and Biophysics vol. 83, 70-77 (1959).

Frost, Megan C. et al., "Synthesis, Characterization, and Controlled Nitric Oxide Release from S-Nitrosothiol-Deriyatized Fumed Silica Polymer Fifer Particles", Copyright 2005, Wiley Periodicals, Inc., pp. 409-419.

Herm, Zoey R. et al., "Metal—Organic Frameworks as Adsorbents for Hydrogen Purification and Precombustion Carbon Dioxide Capture", Journal of the American Chemical Society, Mar. 25, 2011, No. 133, pp. 5664-5667.

*Primary Examiner* — Richard Schnizer
*Assistant Examiner* — Alma Pipic
(74) *Attorney, Agent, or Firm* — Faegre Baker Daniels LLP

(57) ABSTRACT

A polymeric composition capable of releasing nitric oxide and modulating biological responses comprises a biocompatible polymer and S-nitrosated thiol bonded to the biocompatible polymer. The polymeric composition can have a thiol conversion of at least 40%. The polymeric composition can also have a nitric oxide recovery of at least 40% when under thermal decomposition conditions.

16 Claims, 17 Drawing Sheets

Thiol-functionalized NO donors used for polymer modification:

Cysteamine (a)   Cysteine (b)   Homocysteine (c)

where NH$_2$-R-SH represents cysteamine (a) and cysteine (b), and their homologous

MATERIALS FOR MODULATING BIOLOGICAL RESPONSES AND METHODS OF MAKING

CROSS REFERENCE TO RELATED APPLICATIONS

This application claims priority to U.S. Provisional Application No. 61/446,121, filed Feb. 24, 2011, entitled "METHODS FOR MODULATING CELL RESPONSE," the contents of which are hereby incorporated by reference in their entirety.

GOVERNMENT LICENSE

The invention described herein was made with Government support under Grant No. W81XWH-11-2-0113 awarded by the Department of Defense Congressionally Directed Medical Research Program (CDMRP). The government has certain rights in the invention.

TECHNICAL FIELD

The present invention relates generally to modulating biological responses and materials for modulating such responses.

BACKGROUND

In the case of injury, whether a consequence of surgery or from an accident or a mishap, wounds do not heal completely and this often leads to additional health complications. Of the reasons for this is because in would injuries, multiple biochemical pathways are activated and thus in order to achieve complete healing, simultaneous modulation of multiple biological responses is needed, in a similar way in many disease sates, several different cell and protein types are affected. To treat the disease effectively, all of the affected cell types must be treated. This involves developing methods and materials that can effectively modulate multiple biological responses.

As one example, a recent study by the American Academy of Orthopedic Surgeons estimates that over 500,000 bone-grafting surgeries are performed annually. By 2030, an overall incident increase of 600% is predicted in the United States alone. Standard clinical grafting practices to repair bone-tissue damage include autografting, allografting and xenografting. However, these procedures often result in incomplete healing and lead to additional health complications in patients. To overcome these problems, researchers are developing new bone-tissue engineering strategies such as using natural and synthetic materials as scaffolds for repair. A number of these engineered scaffolds are currently available for clinical uses. However, a well-accepted, versatile and clinically-proven scaffold is yet to be fully realized.

Because of the multi-faceted problems associated with wound injuries, it would be ideal for interventions to treat inflammation, thrombosis, infection, and wound healing in one treatment that can be easily applied in a variety of field settings—emergency response, battlefield, hospitals, homes and clinics. An ideal treatment would inhibit multiple consequences of injury, such as inflammation, thrombosis, and infection, without causing systemic effects. At the same time, it would be judicious if the treatment also promoted wound healing processes. In these ways, a method is needed that can modulate multiple cellular responses.

Such as strategy requires (1) the identification of suitable therapeutic agent(s) with short biological half-lives and (2) designer polymers that act as sophisticated drug carriers. The therapeutic agents used to develop these materials should be at least in part agents that are already involved in normal homeostasis. For example, the endothelial cells that line all blood vessel walls have a number of bound therapeutic agents and bioagents that are released from the surface of the endothelial cells that are responsible for maintaining normal homeostasis within the blood. As a result, synthetic materials and methods that have features that replicate the function of the normal endothelium are more likely to provide the ultimate route to safely modulating biological responses. As such, the materials and methods described herein leverage the biological properties of naturally occurring biogents in synthetic materials to control biological responses in order to treat a wide range of diseases or to prevent biofouling or treat injuries associated with a variety of medical devices where localized control of function is only at the fluid-delivery agent interface where action is targeted.

To date, two major classes of synthetic polymers have been explored as materials in these types of applications. The first class includes synthetic biodegradable polymers such as polylactide (PL), polyglycolide (PG), poly(lactide-co-glycolide) (PLGA) and poly($\epsilon$-caprolactone)(PC). These materials are formed into nanoscaffolds using the process of electrospinning. The resulting scaffolds have diameters between 50-500 nm (similar to the size of many naturally occurring fibrous components such as collagen within ECM), high porosities (up to 80%), and large surface areas for cell attachment, bone in-growth, and nutrient transport, making the materials a suitable ECM analogue for tissue engineering applications. However, because these polymers have relative low hydrophilicities and lack cellular recognition, cell affinity to the scaffold to promote osteointegration is significantly diminished. In the end, the scaffold results in poor cell adhesion, migration, proliferation and differentiation.

A second class of biodegradable materials that have been studied for these applications include polysaccharide-grafted polymers. Investigators have demonstrated that these materials have adequate mechanical properties (tensile strength and bending strength) to support tissue growth over natural materials such as collagen. Moreover, the polysaccharides materials have improved cell compatibility and structural integration with many cell adhesion molecules and matrix glycoproteins as compared to the PL and PLGA polymers. For example, chitosan, a naturally available polysaccharide, is structurally similar to glycosaminoglycans (GAGs) present within bones and possesses a number of osteophilic advantages including biocompatibility and biodegradability. Similarly, dextran, a homopolymer of glucose with predominantly $\alpha$-(1→6) linkages has been investigated as a material for tissue scaffolds due to its relative biocompatibility and degradability. The high surface tension of these polysaccharide materials due to their polycationic nature have caused challenges in fabricating nanofibers using electrospinning methods. As a result, composites materials of chitosan have been prepared by blending the polysaccharide with various fiber-forming polymers such as poly(vinyl alcohol), poly(ethylene oxide), poly(vinyl pyrrolidone), poly($\epsilon$-caprolactone) and poly(L-lactic-co-$\epsilon$-caprolactone). The composite materials were then successfully spun into nanofibers. The resulting nanofibers, however had inconsistence mechanical and cell affinities in regions of the scaffold.

Although the synthetic and polysaccharide-derived materials have demonstrated an alternative to autografting, allografting and xenografting, the materials still do not possess all of the requisite biological properties of an ideal material to modulate cellular responses. Specifically, the materials cause activation of the coagulation cascade and provoke the immune response system (i.e., cause inflammation). As shown in FIG. 1, the tissue healing cascade begins immediately following injury and goes through four stages: hemostasis, inflammation, proliferation, and remodeling. First, the coagulation cascade is activated and platelets aggregate around exposed collagen leading to a fibrin clot matrix that leads to eventual healing. Subsequently, a variety of other factors are released including cytokines, platelet-derived growth factor (PDGF) and transforming growth factor-beta (TGF-β) during the inflammatory phase. As a result of this release, neutrophils, macrophages, and lymphocytes are stimulated. The proliferative phase follows and is marked by epithelialization, angiogenesis, and fibroblast growth and results in new connective tissue. In the final phase collagen is cross-linked and scar maturation results. If any part of the healing cascade is perturbed, fibrosis and chronic ulcers may result.

SUMMARY

In one embodiment, a polymeric composition capable of releasing nitric oxide and modulating biological responses comprises a biocompatible polymer and S-nitrosated thiol bonded to the biocompatible polymer. The polymeric composition can have a thiol conversion of at least 40%. The polymeric composition can also have a nitric oxide recovery of at least 40% when under thermal decomposition conditions.

A method of modulating a biological response is also provided. The method includes contacting the subject with a medical device comprising a polymeric material. The polymeric material includes a biocompatible polymer. Functional moieties are bound to the biocompatible polymer and are capable of releasing nitric oxide. The polymeric material has a nitric oxide recovery of at least about 40% under thermal decomposition conditions.

A method of forming a biocompatible polymer capable of releasing nitric oxide for modulating biological responses is also provided. The method includes activating carboxyl groups of the biocompatible polymer in a non-aqueous solution by reaction with NHS and converting thiol residues on the biocompatible polymer to S-nitrosated residues under non-aqueous conditions, wherein the thiol conversion is at least about 40%

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Definitions

Figure 1:
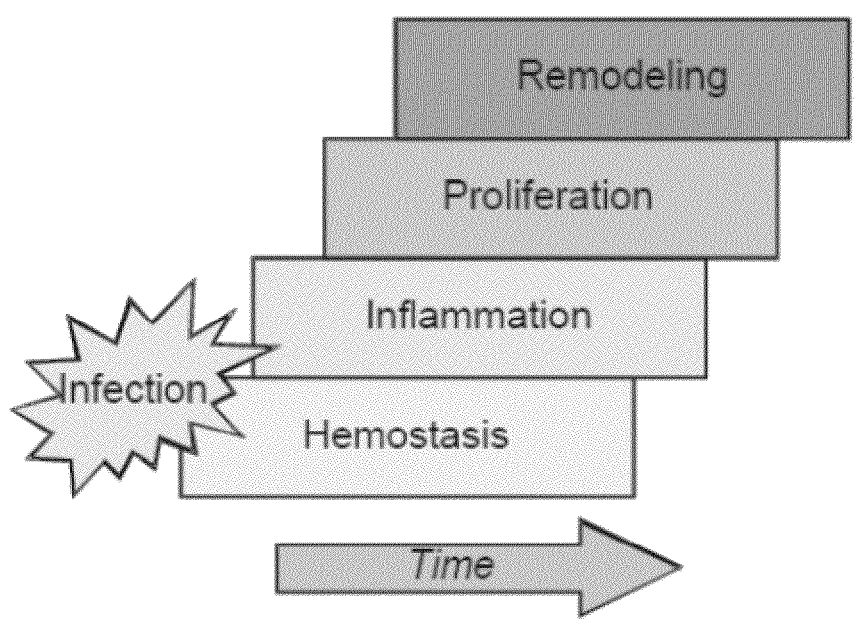
FIG. 1 is a block diagram of a tissue healing cascade.

For convenience, before further description of the present invention, certain terms used in the specification and examples are described here. These definitions should be read in light of the remainder of the disclosure and understood as by a person of skill in the art. Also, the terms "including" (and variants thereof), "such as", "e.g.", "i.e." as used herein are non-limiting and are for illustrative purposes only.

The articles "a" and "an" are used herein to refer to one or to more than one (i.e. to at least one) of the grammatical object of the article. By way of example, "an element" means one element or more than one element.

"Biodegradable" means chemical breakdown of materials by a physiological environment. This can include, but is not limited to physiological fluids such as blood and blood components, subcutaneous fluid, tissue fluid, or urine.

"Biological responses" refers to any biochemical pathways, cells, proteins, DNA, RNA, and other substances in the body that are altered.

"Host-guest" is a term that describes the relationship between a discrete compound ("guest") that is located within the pores or open spaces of a metal-organic compound ("host"). The discrete guest and the metal-organic compound in this relationship are not strongly covalently bonded. In many cases, the discrete guest compound, such as carbon dioxide gas, is stored in the pores and open spaces of the host, such as MOF compounds typically exhibit.

"Porosity" describes the size of the void spaces in a material. The higher the void space compared to material space, the higher the porosity. Porosity can range from 0-100%.

"Encapsulant" or "Encapsulating" refers to surrounding the agent in another material.

"Secondary therapeutic agent" refers to compounds that cause a desirable and beneficial physiological result in response to the compound. Exemplary non-genetic therapeutic agents for use in conjunction with the present invention include, but are not limited to: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, viricristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.). Exemplary genetic therapeutic agents for use in conjunction with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor ÿ and ÿ, platelet-derived endothelial growth factor, platelet-derived growth factor, tumor necrosis factor a, hepatocyte growth factor and insulin-like growth factor, (d) cell cycle inhibitors including CD inhibitors, and (e) thymidine kinase ("TKE") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

"Material" and "matrix" are art recognized and refer to that the metal-organic compounds, therapeutic agents, and secondary therapeutic agents that are contained within. These can include, but are not limited to, plastics, cements, and clays.

"Polymer" is a large molecule composed of repeating structural or constitutional units, usually referred to as monomers, connected by covalent chemical bonds. Polymers can consist of the same or differing repeat units in order or random fashion. Polymers may take on a number of configurations, which may be selected, for example, from cyclic, linear, branched and networked (e.g., crosslinked) configurations. Branched configurations include star-shaped configurations (e.g., configurations in which three or more chains emanate from a single branch point, such as a seed molecule), comb configurations (e.g., configurations having a main chain and a plurality of side chains), dendritic configurations (e.g., arborescent and hyperbranched polymers), and so forth. As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating), and block copolymers.

"Plasticizer" is art recognized is a compound that is added to polymers that increases the plasticity or fluidity of the material to which they are added. Some examples include, but are not limited to, dicarboxylic/tricarboxylic ester-based plasticizers such as dioctyl sebacate (DOS), benzoates, sulfonamides, organophosphates, and glycols, or benzoates.

The terms "blend", "layered", "hybrid", "composite", and "hybrid-composite" are used to describe materials that are made from more than one component and in various combinations.

"Interpenetrating network" (IPN) describes any material containing two macromolecular compounds, such as polymers or metal-organic compounds whose structures interweave and fill the spaces of the other substance by physical means. These networks may or may not have chemical interactions with each other.

"Crystallinity" is art recognized and refers to the ordered structure of the polymer.

"Producing" is a generic term used to describe all mechanisms of delivery including generating and releasing modes.

"Biocompatibility" is a generic term that describes an interaction or relationship with physiological or biological systems.

"Medical device" refers to product which is used for medical purposes in patients, in diagnosis, therapy, treatment, or surgery. If applied to the body, the effect of the medical device can be physical or chemical.

"Bioerodable" refers to the chemical breakdown of material by the physiological environment beginning at the surface of the material.

"Physiological fluid" refers to any fluid produced by the body, including but not limited to, subcutaneous fluid, saliva, blood, extracellular fluid, and urine.

"Processing" refers to manipulation of the material by a physical means. This includes but is not limited to spray coating, extrusion, dip coating, molding, electrospinning, and casting.

"Thermal decomposition conditions" refers to raising the temperature of a sample until all of the nitric oxide releasing moieties have decomposed as evidenced by a baseline NO measurement.

Biodegradable Polymers Capable of Modulating Biological Responses

The present invention includes biodegradable polymers comprised of functional moieties bound to the polymeric backbone that are capable of modulating biological responses, for example, but not limited to, by producing NO. Other examples include the use of other naturally occurring biological agents such as $PGI_2$, thrombomodulin and the like. These functional biological agents can be included into the biodegradable materials as small organic compounds, metal organic frameworks, inorganic compounds, or by non-covalent attachment means Additional embodiments include the combination of polymeric compounds with and without secondary therapeutic agents that are capable of modulating biological responses as well.

Still further embodiments describe compositions of materials comprised of polylactide/polygycolide co-polymers and polysaccharides bound polymers combined with functional groups capable of releasing NO and or other naturally occurring biological agents such as $PGI_2$, thrombomodulin and the like under physiological conditions that modulate biological responses Cells are disrupted when an injury occurs. Previously, drugs or therapeutic agents were provided to injuries in order to prevent undesired biological processes. The current invention uses naturally occurring therapeutic agents or biological agents, such as nitric oxide, in concert with appropriate delivery platforms to provide an effective solution to modulating multiple biological responses, such as cellular and protein behavior, in the treatment of wounds. The current invention provides a therapeutic agent to help damaged cells function properly until they grow back to their healthy function. These goals are achieved by providing a material having a high therapeutic loading and having a high therapeutic agent recovery percentage.

Suitable delivery platforms include biodegradable polymers such as polylactide (PL), polyglycolide (PG), poly(lactide-co-glycolide) (PLGA) and poly(8-caprolactone)(PC). These materials are made by incorporating monomeric units in appropriate ratios that give rise to morphological and biochemical properties. These monomeric units can be post synthetically modified to contain additional therapeutic action. As an example, diazeniumdiolates and S-nitrosothiols are formed on nitrogen and sulfur-based functional groups. The monomer units used to create the biodegradable polymer can be readily modified to incorporate the necessary nitrogen and sulfur based linkers required to allow the structures to be generated that can store and release NO in physiological systems. If multiple therapeutic agents are used, the therapeutic agents can be in the same material layer or different material layers. Not all of the material layers used need to have a therapeutic agent. Each layer of the overall material may contain a unique combination of zero, one, or multiple therapeutic components. Other suitable polymers include polysaccharides, such as but not limited to dextran and chitosan.

Nitric oxide (NO) is a well known naturally-occurring biological agent responsible for maintaining normal hemostasis, cellular signaling, and bone development in the body as well as promoting healthy cell growth and wound healing. Nitric oxide is also responsible for preventing platelet activation and adhesion as well as microbial growth and bacterial invasion of tissue. Nitric oxide also serves as an effecter in wound healing mechanisms, and regulates angiogenesis and revascularization. Most recently, published reports have demonstrated that NO produced by the endothelial NO synthase (eNOS) also plays an important role in bone development and healing as an inducer of osteoblastic differentiation (bone formation) especially in mesenchymal progenitor cells. Mesenchymal progenitor cells promote mineralization, stimulate expression in fibroblasts, enhancing osteoclast activities and inhibiting bone resorption. Moreover, alleviation of osteoporotic bone loss by administration of exogenous NO donors provided a better choice for osteoporosis therapy compared to conventional therapies. Previous work has shown that functional moieties capable of releasing NO in vivo increase the hemocompatibility of materials by reducing the thrombogenicity. In addition, the release of NO reduces the inflammatory response towards the implanted materials. Further, nitric oxide has multiple biphasic effects on cells. For example, nitric oxide's role in tumor biology includes angiogenesis and metastasis, and modulation of both necrosis and apoptosis. Thus, nitric oxide has the capability of treating abnormal cell growth while at the same time promoting the healing of surrounding cells. Due to nitric oxide's multiple effects of cells, the incorporation of functional moieties capable for releasing nitric oxide under physiological conditions can impart several advantages to modulating multiple biological processes resulting in healthy incorporation of medical devices into the body, reduction in infection, thrombosis, and monocyte activation, improvement in wound healing at the site of injury, and metathesis of cancerous cells.

As discussed above, the polymeric composition is capable of releasing nitric oxide and modulating biological responses. The polymeric composition may be capable of modulating biological responses at least in part due to the polymeric composition having a high nitric oxide loading. For example, the polymeric composition may have a nitric oxide loader greater than 0.1 mmol/g polymer, greater than 0.2 mmol/g polymer, greater than 0.3 mmol/g polymer, greater than 0.4 mmol/g polymer or greater than 0.5 mmol/g polymer. The high nitric oxide loading enables nitric oxide release over a longer time frame. In one example, nitric oxide is released over a period of at least 172 hours. The nitric oxide loading and release time frame enable therapeutic dosages of nitric oxide that modulate biological responses, not just inhibit consequences of injury (e.g., inflammation, thrombosis, and infection).

The polymeric composition also has a relatively high nitric oxide recovery percentage, which can be calculated by measuring the nitric oxide released during a given period compared to the equivalent nitric oxide present in the initial polymer. Suitable polymeric compositions have a nitric oxide recovery of at least about 40%, at least about 50%, at least about 60%, at least about 70% or at least about 80%, under thermal dry conditions (step-wise heating up to 100° C. until base line levels of NO are reached). Under physiological conditions (10 mM PBS buffer, pH 7.4, 37° C.) for 48 hours, suitable polymeric compositions have a nitric oxide recovery of at least about 20%, at least about 25%, at least about 30%, at least about 40% or at least about 50%. Under physiological conditions (10 mM PBS buffer, pH 7.4, 37° C.) suitable polymeric compositions have a nitric oxide recovery of at least 70%, at least 75%, or at least 80% if allowed to go to competition.

In one example the polymeric composition includes a biocompatible polymer, such as a biodegradable polymer or a polysaccharide, and S-nitrosated thiol bonded to the biocompatible polymer. The polymeric composition can be synthesized to include thiol residues. In one example at least 40% of the thiol residues are converted to S-nitrosated thiol (e.g., a thiol conversion of at least 40%). In another example, the polymeric compositions has a thiol conversion of at least 50%, 60%, 70%, 80%, 90%. In other examples the thiol conversion can be as great as 100%.

In one example, the thiol residue is selected from the group consisting of residue of a thiol or an amino-thiol. In another example the thiol residue is selected from the group consisting of cysteamine, cysteine, and homocysteine residues and combinations thereof. In a still further example, the thiol residue is selected from the group consisting of glutathione or penicillamine.

Methods of making suitable polymeric compositions are also provided. In one example, the polymeric compositions are synthesized with a non-aqueous method. For example, the synthesis method may include activating carboxyl groups of the biocompatible polymer in a non-aqueous solution by reaction with N-hydroxysuccinimide (NHS), adding a thiol to the biocompatible polymer to attach thiol residues onto the backbone of the biocompatible polymer, and converting the thiol residues to S-nitrosated residues under non-aqueous conditions. In one example at least about 40% of the thiol residues are converted to S-nitrosated residues (i.e., a thiol conversion of at least about 40%).

After synthesis, the polymeric compositions can be processed into a final form, such as a polymer film, nanofibers, or multilayer coatings. Typically, polymeric compositions can lose nitric oxide capacity during processing. The polymers and their processing in these ways remain stable. Processing the polymeric compositions into different engineered forms, achieves a higher NO release rate than previously believed possible. The time period over which the NO is released from the processed polymeric compositions is also longer than previously achieved. This may be due to higher surfaces areas, changes in surface morphology or wettability, access of fluids (either water or other physiological fluids (i.e., blood, stomach fluid, interstitial fluid, etc.) or cells to the material interface.

In one example, polymeric materials prepared above can be electrospun into fibers. In brief, polymer solutions in a suitable solvent are ejected from the tip of a fine nozzle of a syringe, maintained at a high DC potential. Using a syringe pump, a constant flow of the fluid will be maintained and once the electrostatic repelling force of the charges overcomes the surface tension of the solution droplet, the charges leave the droplet and drag the polymer into thin fibers. Finally because of unstable whip-like motions, these fibers will further reduce their diameter and elongate into nanofibers.

The polymeric materials can be electrospun to produce micro and nanoscaffolds for treating bone repair injuries or tissue injuries with enhanced bone development and healing capability with distinct and multifaceted mode of actions. Scanning electron micrographs (SEMs) demonstrating the ability to electrospin the materials are given in FIG. 3.

The polymeric materials can be prepared as biodegradable transdermal patches for wound healing.

The polymeric materials can be prepared as biodegradable anti-inflammatory surgical threads or other implanted devices such as stents.

The polymeric materials can be processed into macrocapsules or microspheres. One such strategy is to dissolve S-nitrosated dextran derivatives in a suitable solvent like dimethyl sulfoxide (DMSO) and then emulsified in a large excess of non-soluble solvent such as hexane, heptane etc. in presence of a suitable emulsifying agent such as tween-20.

Further, in a composition embodiment, the therapeutic biodegradable materials are incorporated into another material, such as a polymer. In some embodiments, the material can be a polymer that has additional chemical functionalities such as, but not limited to, amine, carboxyl, halide, ketone, urethane, urea, silicone, or aldehyde groups. The material can also have differing degrees of porosity or diffusion characteristics. Other compositions of the invention include encapsulating the biodegradable polymers into other materials such as polymers or using the biodegradable polymer as encapsulants for other therapeutics (i.e., drugs). These drugs may have the form of a metal organic framework or an organic structure. Other compositions may include adding a secondary therapeutic agent to the material in concert with the biodegradable polymer that produces nitric oxide. The secondary therapeutic agent could be covalently attached to the metal-organic compound, blended with the biodegradable polymer, or blended into another material such as an organic polymer. The secondary therapeutic agent may also be covalently attached to the biodegradable polymer or nonspecifically bound to the biodegradable polymer.

Additional compositions may include, but are not limited to, using the biodegradable polymers in conjunction with synthetic polymers such as polyurethane (PU), polyesters, polyethers, silicones, silicates, poly(vinyl chloride) (PVC), acrylates, methacylates, dextran, synthetic rubber (cis-polyisoprene), polyvinyl acetate, Bakelite, polychloroprene (neoprene), nylon, polystyrene, polyethylene, polypropylene, polyacrylonitrile, polyvinyl butyral (PVB), poly(vinylidene chloride), or fluorinated polymers such as polytetrafluoroethylene (PTFE) where either or both of the metal-organic compounds and secondary therapeutic agents are incorporated. These synthetic materials can be used as homopolymers or multi-component polymers (i.e., copolymer, tri-polymers, etc.). The polymers may be hydrophobic or hydrophilic or contain regions of both hydrophobicity and hydrophilicity.

The composition can also include natural polymers such as DNA, phosphodiesters, polysaccharides, or glycosides where either or both of the therapeutic biodegradable polymers and secondary therapeutic agents are incorporated.

The composition may also include other biodegradable or bioerodable polymers in whole or in part of the final material formulation. Example of biodegradable or bioerodable polymers may include, but are not limited to, polyesteramides, polyglycolide, polyanhydrides, polyorthoesters, ureas, urethanes, esters, ethers, polyhydroxybutyrate (PHB), polyhydroxyvaleratepolylactide, poly(-caprolactone), polyiminocarbonate, poly(dioxanone), polyarylates, as well as copolymers of these and other monomers such as -caprolactone with dl-lactide, -caprolactone with glycolide, lactide with glycolide, and glycolide with trimethylene carbonate (TMC) Amino acid based polymers such as tyrosine-derived polycarbonates are also included.

The composition may also include fibrous matrices, composite materials, layering, particles or blends. Nano- or micro-particles of the matrix material incorporated with secondary therapeutic agents used either alone or in combination with another matrix material are included. For example, the therapeutic biodegradable polymer can be encapsulated into a biodegradable cellulose material which is then delivered orally or is blended into another polymer matrix such as polyurethane and used as a permanent coating implant.

The polymeric materials can be further blended with plasticizers to make composite compositions to tailor the release rates and elasticity of the final polymeric material.

Compositions, configurations, and uses of this invention have the mechanical properties that match the application such that the material in its final embodiment remains sufficiently strong until the surrounding tissue has healed, does not invoke an inflammatory or toxic response, and for biodegradable application is metabolized in the body after fulfilling its purpose, leaving no trace. Further, the material is easily processed into the final product form, demonstrates acceptable shelf life, and is sterilized by acceptable methods such as ethylene oxide, gamma, or auto-clave.

Matrix materials for use in this invention can have various degrees of crystalline or amorphous character, ranging from 100% crystalline to 100% amorphous. The material can have a range of differing microdomains and morphologies that aid in the final application. The matrix materials can also be used in this invention regardless of their stereochemistry. Both region- and stereoisomerization forms of the matrix material can be used. For example, the invention can be practiced using polymers with multiple stereochemical forms such as isotactic, syndiotactic, and atactic.

Also included in this disclosure is a method for treating diseases, disorders, or conditions in a patient using therapeutically effective amounts of the described composition. These diseases, disorders, or conditions may be present in the patient prior to treatment as well as caused by the procedure or the placement of the medical device. As used herein, "treatment" refers to the prevention of a disease or condition, the reduction or elimination of symptoms associated with a disease or condition, or the substantial or complete elimination of a disease or condition.

Diseases, disorders or conditions may include, but are not limited to, tumors, organs including the heart, coronary and peripheral vascular system (referred to overall as "the vasculature"), the urogenital system, including kidneys, bladder, urethra, ureters, prostate, vagina, uterus and ovaries, eyes, ears, spine, nervous system, lungs, trachea, esophagus, intestines, stomach, brain, liver and pancreas, skeletal muscle, smooth muscle, breast, dermal tissue, cartilage, tooth, bone, local infection, systemic infection, biofouling, macrophage formation, heart disease, artery and vein damage or disease, tissue injury, vascular legions, initimal hyperplasia, heart failure, high or elevated blood pressure, vasoconstriction, platelet adhesion, platelet aggregation, atherosclerosis, thromboembolism, thrombosis, smooth muscle cell proliferation, sepsis, complications with medical devices, wounds caused by initicions or insertion of medical devices, cicatrices, endothelial cell damage, arrhythmias, heart defects, congenital heart defects, cell overgrowth, and soft bones. The compositions described herein can be used to promote angiogenesis, delivery of analytes to the site of injury, and perfusion of blood to the site of injury. The compositions can also be used to regulate the coagulation cascade.

Compositions further include, but are not limited to, administration as clinically prescribed including intravenously, orally, bucally, parenterally, inhalation spray, topically either within conjunction with a delivery vehicle (i.e., bandage or gel) or alone, locally, and transdermally.

Local delivery includes any means by which the composition can be made in contact with the targeted delivery site in the patient including, but not limited to, sutures, bandages, patches, wraps, vascular implants, stents, drug pumps, catheters, guidewires or any other implantable medical devices.

The disclosure also includes a medical device that comprises the composition described herein. Such a medical device includes, but are not limited to, catheters (e.g., urological or vascular catheters such as balloon catheters and various central venous catheters), guide wires, balloons, filters (e.g., vena cava filters and mesh filters for distil protection devices), stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, embolization devices including cerebral aneurysm filler coils (including Guglilmi detachable coils and metal coils), embolic agents, hermetic sealants, septal defect closure devices, myocardial plugs, patches, pacemakers, lead coatings including coatings for pacemaker leads, defibrillation leads, and coils, ventricular assist devices including left ventricular assist hearts and pumps, total artificial hearts, shunts, an interventional cardiology device, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, orthopedic prosthesis such as bone grafts, bone plates, joint prostheses, orthopedic fixation devices such as interference screws in the ankle, knee, and hand areas, tacks for ligament attachment and meniscal repair, rods and pins for fracture fixation, screws and plates for craniomaxillofacial repair, dental implants, plastic tubing, a dialysis bag or membrane, a ventricular shunt, an external device applied directed to the skin as well as various other devices that are implanted or inserted into the body and from which therapeutic agent is released.

The medical device made be coated or completely fabricated from the matrices.

As discussed above, the composition may be incorporated into a tissue-engineered scaffold. The tissue-engineered scaffold can provide mechanical support for tissue growth coupled with naturally produced biological mediators that promote healing. As such, the scaffold can be porous for nutrient transport, hydrophilic for cell attachment, biodegradable as the native tissue integrates, encourage bone cell migration into a defect (osteoconduction), support and promote osteogenic differentiation (osteoinduction), enhance cellular activity towards scaffold-host tissue integration (osteointegration), present a physicochemical biomimetic environment and actively promote or prevent desirable and undesirable physiological responses. Further the scaffold material can mimic the nanotopography and functionality of the extracellular matrix (ECM) and make use of biologically derived mediators to successfully regenerate damaged tissue.

EXAMPLES

The present invention is more particularly described in the following examples that are intended as illustrations only, since numerous modifications and variations within the scope of the present invention will be apparent to those of skill in the art. Unless otherwise noted, all parts, percentages, and ratios reported in the following examples are on a weight bases, and all reagents used in the examples were obtained, or are available, from the chemical suppliers described below, or may be synthesized by conventional techniques.

Example 1

Figure 2:
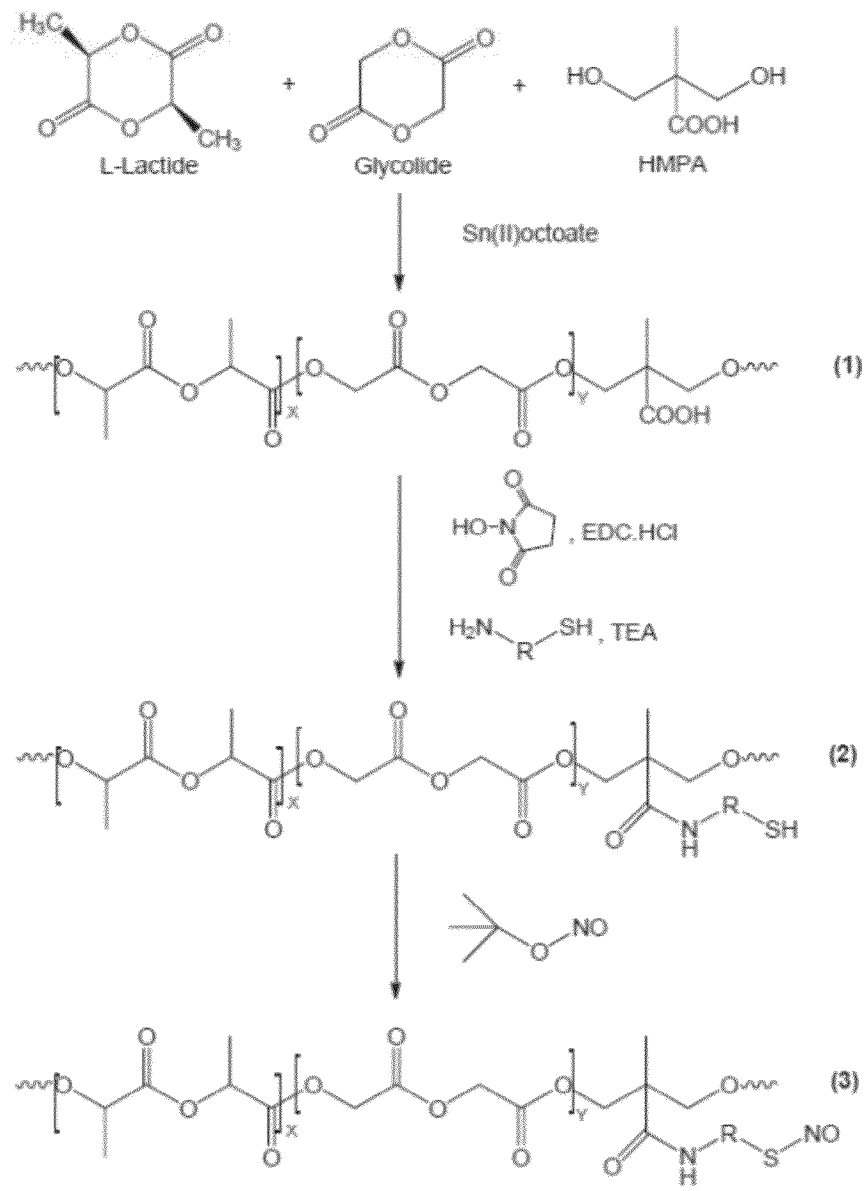
FIG. 2 illustrates the synthesis of S-nitrosated PLGH polymers.
Figure 2:
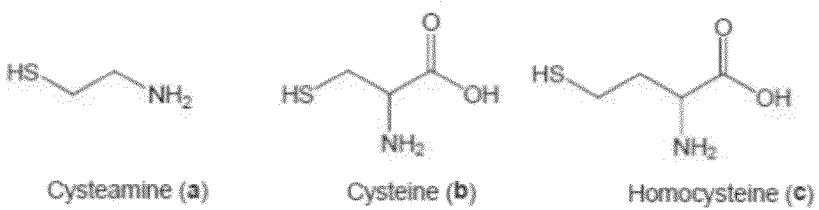

Nitric Oxide Releasing S-nitrosated poly(lactic-co-glycolic-co-hydroxymethyl Propionic Acid) (PLGH) Polymers FIG. 2 is a scheme for preparing S-nitrosated PLGH polymers.

PLGH (1): L-lactide (1.7 g, 85% w/w), glycolide (0.2 g, 10% w/w), 2,2-bis(hydroxymethyl)-propionic acid (HMPA, 0.1 g, 5% w/w) and stannous octoate (0.01 g, 5% w/w of total polymer) were mixed with 2 mL dry dichloromethane (DCM, freshly distilled using calcium hydride) in a polymerization tube under nitrogen. Solvent was removed under vacuum and applied nitrogen and vacuum alternatively several times to remove any adhered moisture before heating the mass to 70° C. in an oil bath. Vacuum was again applied for half hour at 70° C. and then replaced with nitrogen and heated to 120° C. to perform the polymerization in the melt phase. After 24 hour, the polymerized material was cooled to room temperature and crystallized using dichloromethane-diethyl ether mixture (1:20) to remove any unreacted monomers. Yield 1.67 g (83.5%). $^1$H NMR (CDCl$_3$): δ 5.17 (m, —O—CH(CH$_3$)—CO—), 1.56 (d, —O—CH(CH$_3$)—CO—), 4.58-4.92 (m, —O—CH—CO—), 4.18-4.40 (m, —O—CH$_2$—C—) and 1.27 (s, —CH$_2$—C(CH$_3$)—).

PLGH-cysteamine (2a): Carboxyl functionalized PLGH intermediate (1) (1.0 g, 0.62 mmol COOH g$^{-1}$ polymer) and N-hydroxysuccinimide (NHS, 0.18 g, 1.55 mmol, 2.5 molar eq.) were mixed together in 4 mL anhydrous dimethylformamide (DMF) under an N$_2$ atmosphere. A solution of 1-ethyl-3-(3-dimethylaminopropyl)carbodiimide hydrochloride (EDC.HCl, 0.3 g, 1.55 mmol, 2.5 molar eq.) in DMF (6 mL) was slowly added using a pressure-equalized addition funnel and maintained the mass at 20° C. for 24 hour to complete the activation of all available carboxyl groups. 0.35 g cysteamine hydrochloride (3.1 mmol, 5 molar eq. of COOH) was dried separately in 12 mL anhydrous DMF under vacuum for two hour to remove any moisture and then mixed with triethylamine (0.47 g, 4.68 mmol, 1.6 molar eq. of cysteamine hydrochloride). The resulted neutralized cysteamine was slowly charged into the NHS activated polymer under N$_2$ and further stirred for 48 hour. The polymer solution was then concentrated under vacuum to remove DMF and the crude product was precipitated out by adding excess diethyl ether and dried under vacuum. The crude product was then redissolved in DCM (25 mL) and washed two times with saturated sodium chloride solution (5 mL) to remove excess cysteamine and to hydrolyze unreacted NHS ester groups. The clear DCM extract was separated and stirred with 50 mg dithiothreitol (DTT) for half hour to reduce any possibly formed disulfide bonds. The DCM extract was again washed two times with saturated sodium chloride solution (5 mL), demoisturised using anhydrous sodium sulphate and filtered through celite to remove any undissolved particles. The product was isolated after distilling the solvent and crystallized using excess diethyl ether. Yield 0.96 g (60%). $^1$H NMR (CDCl$_3$): δ 3.09 (m, —NH—CH$_2$—CH$_2$—) and 2.64 (m, —NH—CH$_2$—CH$_2$—).

PLGH-cysteine (2b): Experiments were performed following the method given for 2a using a mixture of 0.38 g vacuum dried cysteine (3.1 mmol, 5 molar eq.) and 0.16 g triethylamine (1.55 mmol, 2.5 molar eq.) in anhydrous DMF. Yield 0.6 g (60% w/w). $^1$H NMR (CDCl$_3$): δ 5.14 (m, —OCH(CH$_3$)-CO-), 1.55 (d, —O—CH(CH$_3$)—CO—), 4.57-4.89 (m, —O—CH—CO—), 4.23-4.39 (m, —O—CH$_2$—C—), 1.27 (s, —CH$_2$—C(CH$_3$)—) and 3.07 (m, —NH—CH$_2$—SH).

PLGH-homocysteine (2c): Experiments were performed following the method given for 2a and 2b using a mixture of 0.44 g vacuum dried homocysteine (3.1 mmol, 5 molar eq.) and 0.16 g triethylamine in anhydrous DMF. Yield 0.6 g (60% w/w). $^1$H NMR (CDCl$_3$): δ 5.17 (m, —O—CH(CH$_3$)—CO—), 1.56 (d, —O—CH(CH$_3$)—CO—), 4.58-4.92 (m, —O—CH—CO—), 4.18-4.40 (m, —O—CH$_2$—C—), 1.27 (s, —CH$_2$—C(CH$_3$)—), 2.12 (m, —NH—CH$_2$—CH$_2$—) and 2.51 (m, —NH—CH$_2$—CH$_2$—).

S-nitrosated PLGH-cysteamine (3a): 50 mg PLGH-cysteamine (2a) was dissolved in 2 mL dichloromethane-methanol (1:2) mixture in an amber colored EPA vial (Fisher Scientific, NJ). In a separate vial, a solution of 8.4 mg t-butyl nitrite (4 molar eq., pre-treated with 10% w/v disodium ethylenediamine tetraacetate dehydrate (EDTA-disodium salt)) in 1 mL dichloromethane-methanol (1:2) mixture was prepared and added into the polymer solution protected from direct exposure to light. The solution was stirred at 20° C. for 4 hour and then concentrated under vacuum to isolate the S-nitrosated product. UV-vis λmax (2 MeOH: 1 DCM): 338 nm (ε=766.0±19.7 M$^{-1}$ cm$^{-1}$).

S-nitrosated PLGH-cysteine (3b): A 50 mg sample of PLGH-cysteine (2b) was dissolved in a 2 mL methanol:dichloromethane (2:1) mixture in an amber colored EPA vial. In a separate vial, a solution of 8.4 mg t-butyl nitrite (4 molar eq., pretreated with 10% w/v EDTA disodium salt) in 1 mL methanol:dichloromethane (2:1) mixture was prepared and added into the polymer solution while protected from direct exposure to light. The solution was stirred at 20° C. for 8 h and then concentrated under vacuum to isolate the S-nitrosated product. UV-vis λmax (2 MeOH: 1 DCM): 335 nm (ε=882.9±18.2 M$^{-1}$ cm$^{-1}$).

S-nitrosated PLGH-homocysteine (3c): A 50 mg sample of PLGH-homocysteine (2c) was dissolved in a 2 mL methanol:dichloromethane (2:1) mixture in an amber colored EPA vial. In a separate vial, a solution of 8.4 mg t-butyl nitrite (4 molar eq., pre-treated with 10% w/v EDTA disodium salt) in 1 mL methanol:dichloromethane (2:1) mixture was prepared and added into the polymer solution while protected from direct exposure to light. The solution was stirred at 20° C. for 4 h and then concentrated under vacuum to isolate the S-nitrosated product. UV-vis λmax (2 MeOH: 1 DCM): 336 nm (ε=652.1±16.7 M$^{-1}$ cm$^{-1}$).

Example 2

Processed S-Nitrosated PLGH Polymers

The S-nitrosated PLGH polymers of Example 1 were processed into a polymer film or a nanofiber.

S-nitrosated polymer films were prepared on pre-cleaned glass slides by spin-coating a 100 mg/mL polymer solution in dry dichloromethane at a speed of 5000 rpm for one minute using SCS spin coater (Spincoat G3P-8), shielded from direct exposure to light.

Nanofibers were prepared as follows. PLGH, its thiolated derivatives, and the S-nitrosated derivatives were dissolved in a 75:25 w/w mixture of THF and DMF to obtain 10-40 w/w % solutions. The polymer solution was drawn into nanofibers by using electrospinning process. A 1 mL syringe with a 22 G blunt tip needle was loaded with polymer solution and inserted into a variable speed syringe pump (Kent Scientific Corp., Torrington, Conn., USA) with a flow rate of 0.2 mL h$^{-1}$. A 10 kV potential was applied via a high-voltage power supply (Gamma High Voltage Research, Ormond Beach, Fla., USA). Fibers were collected on glass slides attached to a grounded copper plate. Fiber morphology was determined by scanning electron microscopy (JEOL JSM-6500F, JEOL USA, Peabody, Mass., USA), after sputter coating with 10 nm of gold prior to analysis.

Figure 3:
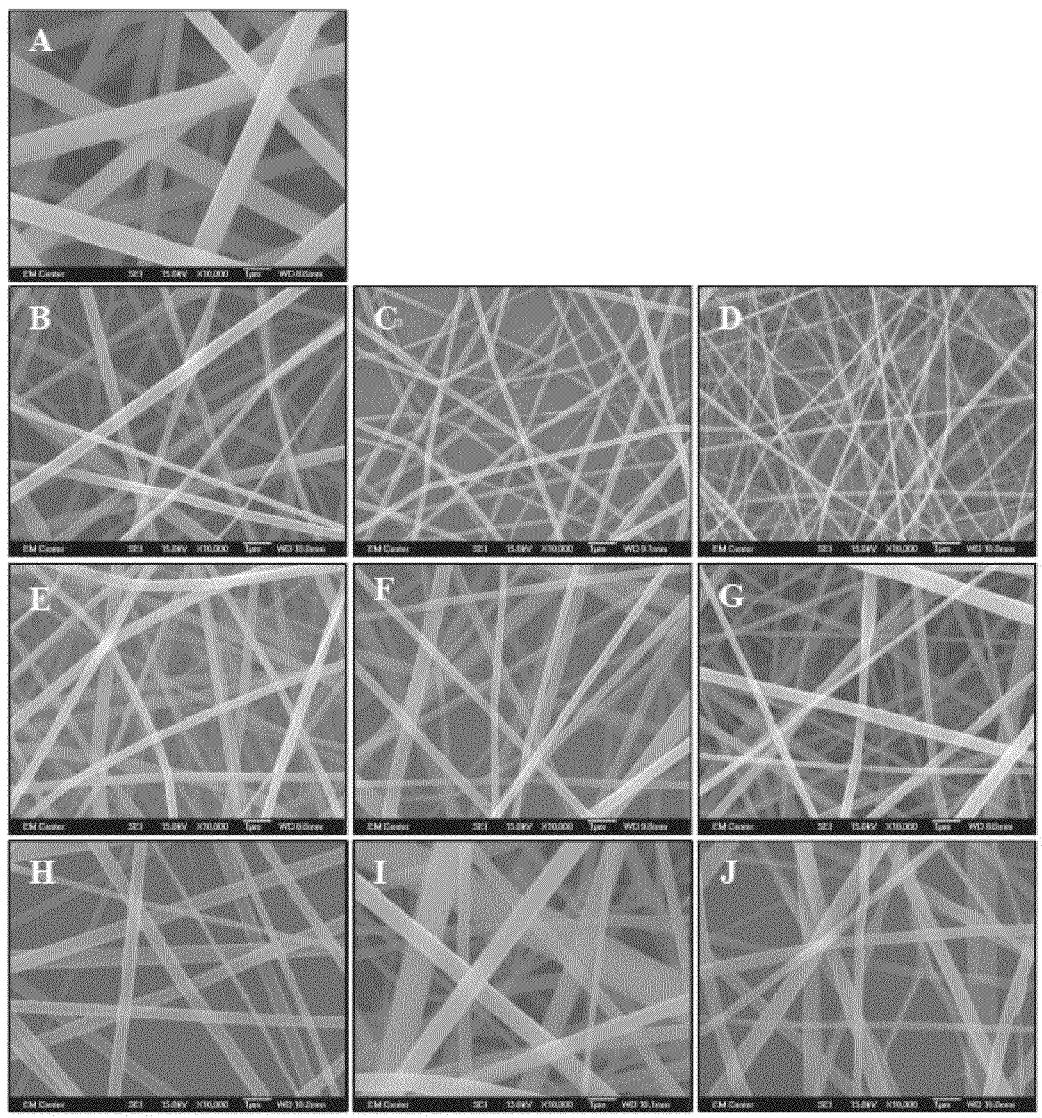
FIG. 3 are SEM images of electrospun nanofibers of (A) PLGH, (B) PLGH-cysteamine, (C) PLGH-cysteine, (D) PLGH-homocysteine, (E) S-nitrosated PLGH-cysteamine, (F) S-nitrosated PLGH-cysteine, (G) S-nitrosated PLGH-homocysteine, (H) S-nitrosated PLGH-cysteamine after NO release, 48 h, (I) S-nitrosated PLGH-cysteine after NO release, 48 h, and (J) S-nitrosated PLGH-homocysteine after NO release, 48 h.

FIG. 3 is SEM images of electrospun nanofibers of (A) PLGH, (B) PLGH-cysteamine, (C) PLGH-cysteine, (D) PLGH-homocysteine, (E) S-nitrosated PLGH-cysteamine, (F) S-nitrosated PLGH-cysteine, (G) S-nitrosated PLGH-homocysteine, (H) S-nitrosated PLGH-cysteamine after NO release, 48 h, (I) S-nitrosated PLGH-cysteine after NO release, 48 h, and (J) S-nitrosated PLGH-homocysteine after NO release, 48 h.

Example 3

NO Release from the Processed S-Nitrosated PLGH Polymers

Real-time NO release from the processed S-nitrosated PLGH polymers of Example 3 was analyzed using Sievers chemiluminescence NO Analyzers® (NOA 280i, GE Analytical, Boulder, Colo., USA). The instrument was calibrated before each analysis using nitrogen as the zero gas and a 45 ppm NO gas. NO release from the S-nitrosated polymer samples was analyzed in deoxygenated 10 mM PBS buffer (pH 7.4) at 37° C., shielded from direct exposure to light. NO release measurements were recorded from all S-nitrosated PLGH polymers using both polymer film and nanofiber forms. Experiments were repeated in triplicate at a data interval of 5 sec at a sampling rate of 200 mL min$^{-1}$ with a cell pressure of 9.7 Torr and an oxygen pressure of 6 psig. Representative NO release profile from the polymer film and nanofiber forms in PBS (10 mM, pH 7.4) and 37 degrees Celsius are given in FIGS. 4 and 5 respectively.

Figure 4:
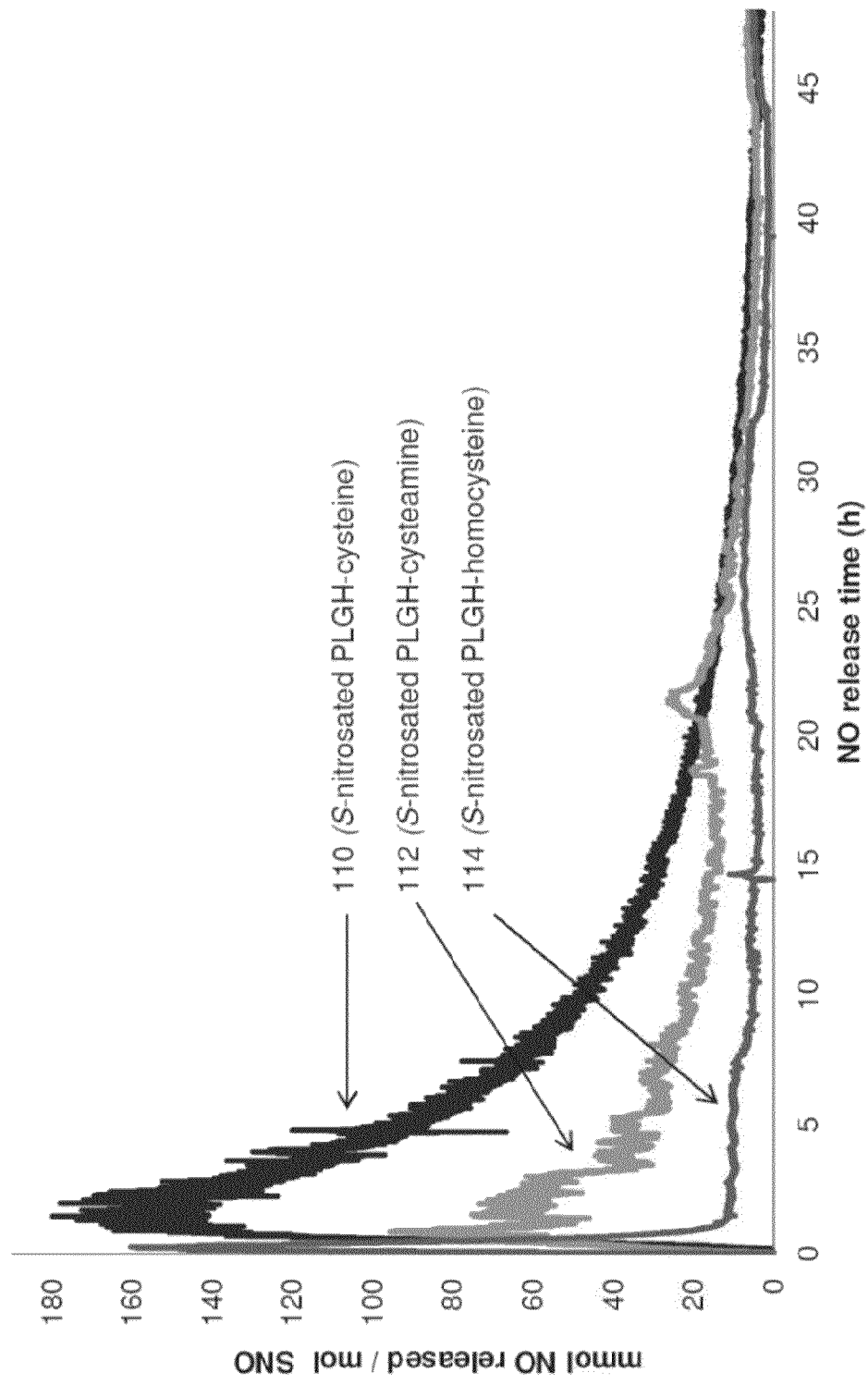
FIG. 4 is a graph illustrating the real-time nitric oxide (NO release) profiles from individual S-nitrosated polymers using polymer films under physiological conditions (10 mM PBS buffer/pH 7.4/37° C.) for 48 h.

In FIG. 4, line 110 represents the NO release profile from the nitrosated PLGH-cysteine polymer in film form, line 112 represents the NO release profile from the nitrosated PLGH-cysteamine polymer in film form, and line 114 represents the NO release profile from the nitrosated PLGH-homocysteine polymer in film form.

Figure 5:
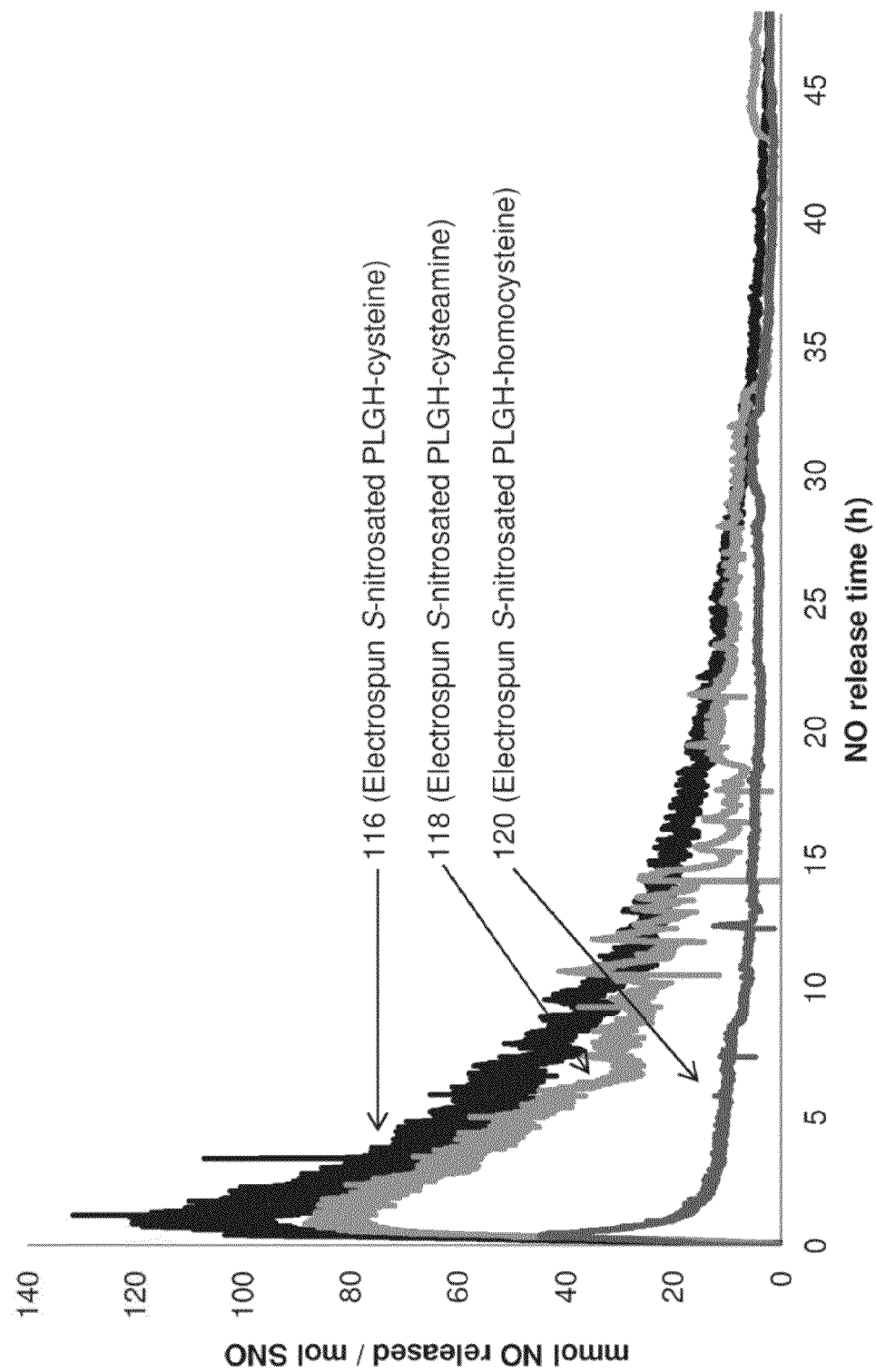
FIG. 5 is a graph illustrating NO release profiles from individual electrospun S-nitrosated polymers under physiological conditions (10 mM PBS buffer/pH 7.4/37° C.) for 48 h.

In FIG. 5, line 116 represents the NO release profile from electrospun nitrosated PLGH-cysteine polymer, line 118 represents the NO release profile from electrospun nitrosated PLGH-cysteamine polymer, and line 120 represents the NO release profile from electrospun nitrosated PLGH-homocysteine polymer. All polymers in FIGS. 3 and 4 were tested under physiological conditions (10 mM PBS buffer, pH 7.4, 37 degrees Celsius) for 48 hours.

FIGS. 4 and 5 illustrate higher and extended NO release rates, which may be achieved in part due to a higher thiol conversion. Higher and extended NO release rates enable a smaller mass of material to be used to achieve similar results. This is important for applications where having small thicknesses is important to prevent (i.e. stent coatings) or for applications where thin coatings are needed to preserve the underlying mechanical properties of the device but thin coatings could limit drug loading.

Example 4

In Vitro Degradation Profiles of the S-Nitrosated PLGH Polymers

Figure 6:
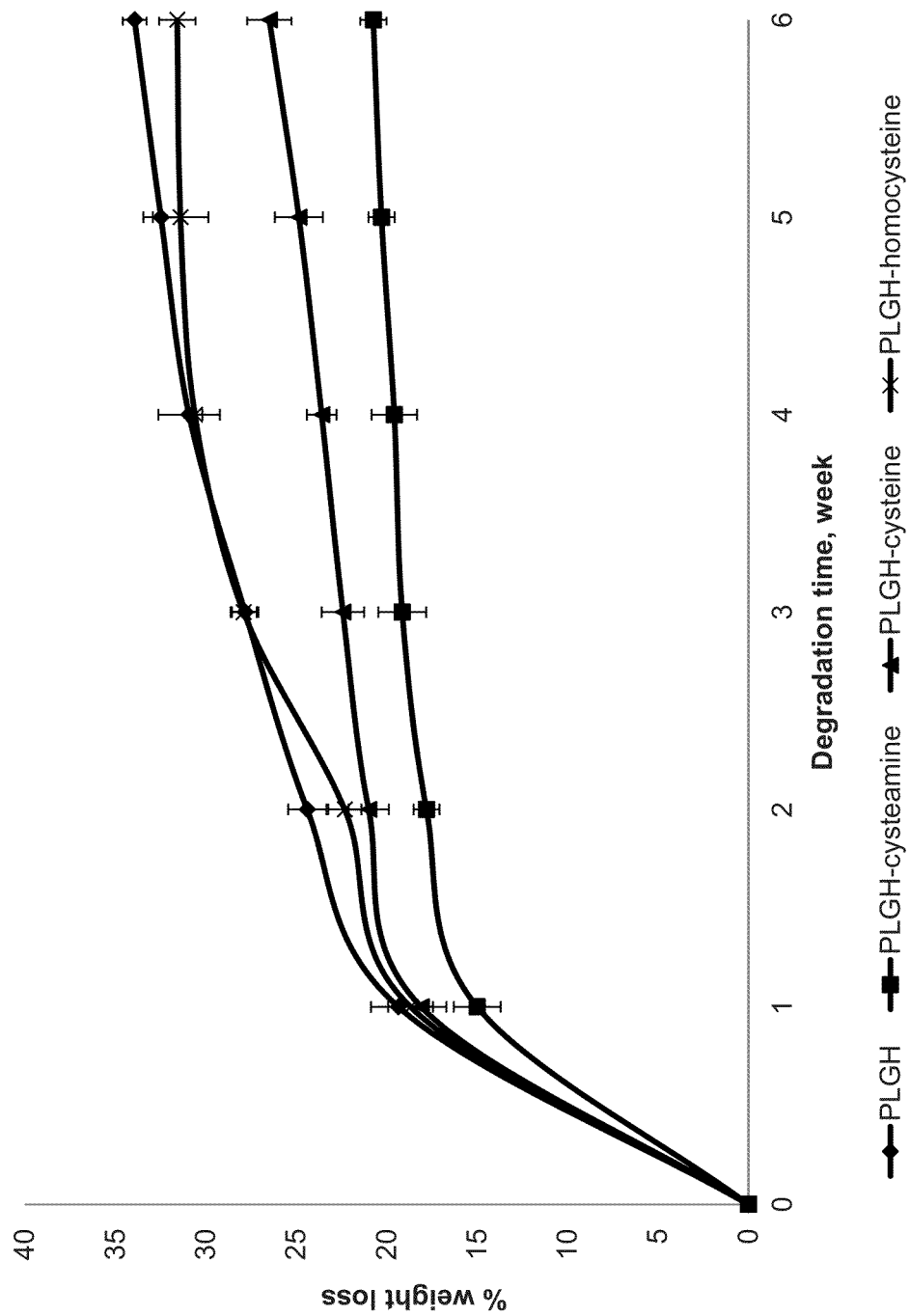
FIG. 6 illustrates a vitro degradation profile of PLGH polymers in 10 mM PBS buffer (pH 7.4, 37° C.).

In vitro degradation profiles of the S-nitrated PLGH polymers of Example 1 were determined by treating the polymers with PBS buffer at 37° C. The degradation profile was monitored by following the percentage weight loss. Buffer solutions were replaced weekly and polymer samples were separated, washed with DI water and dried under vacuum till reaching a constant weight. FIG. 6 illustrates the In vitro degradation profile of PLGH, PLGH-cysteine, PLGH-cysteamine, and PLGH-homocysteine polymers in 10 mM PBS buffer (pH 7.4, 37° C.).

For a wide range of applications, materials are needed that provide local drug delivery (i.e., NO release) to modulate cell/protein behaviors, but are then no longer needed. Thus, a material that can both provide local drug delivery and degradation are important. The NO release profiles (FIGS. 4 and 5) are significant to control many needed biological functions. FIG. 6 shows that the material begins to degrade significantly after the NO release is completed. For tissue engineering or wound healing applications, the timeframe until the material begins to degrade is ideal for supporting initial cell growth as well.

Example 5

Nitric Oxide Loading and Thiol Conversion

S-nitrosated PLGH-cysteamine, PLGH-Cysteine and PLGH-homocysteine polymers were prepared as described in Example 1. The thiol incorporation was calculated by integrating the NMR intensities of the thiol protons and those of the PLGH backbone. The ratio of the average NMR proton intensities between the corresponding thiol protons with that from the HMPA segment of the polymer backbone gives the extent of thiol modification to the polymers.

Nitric oxide loading was experimentally determined using UV absorption spectroscopy. In brief, the intensity of the characteristic absorbance between 335 and 338 nm was measured for each polymer. The concentration was determined from the absorbance intensity and the molar extinction coefficient using Beer's Law. The extinction coefficients were experimentally determined for each polymer and are reported Example 1. The percent thiol conversion was calculated as the nitric oxide content divided by the thiol content.

Table 1 provides the thiol content and thiol conversion (i.e., nitric oxide loading).

TABLE 1

| Polymer | Thiol content mmol SH/g polymer | NO loading mmol SNO/g polymer | % conversion |
|---|---|---|---|
| PLGH-cysteamine | 0.57 ± 0.03 | 0.53 ± 0.01 | 93 ± 3 |
| PLGH-cysteine | 0.39 ± 0.02 | 0.17 ± 0.01 | 43 ± 1 |
| PLGH-homocysteine | 0.18 ± 0.05 | 0.17 ± 0.01 | 96 ± 3 |

High thiol conversion to form S-nitrosothiols are achieved using the non-aqueous nitrosation reaction condition of Example 1. As shown in Table 1, PLGH-cysteamine had a thiol conversion of 93%, PLGH-cysteine had a thiol conversion of 43%, and PLGH-homocysteine had a thiol conversion of 96%.

Example 6

Nitric Oxide Loading and Recovery

The S-nitrosated polymers of Example 5 were further tested to determine the nitric oxide recovery.

Nitric oxide recovery was determined for each polymer using thermal dry test conditions. The samples were heated up to 100 degrees Celsius and the nitric oxide release was determined using Sievers chemiluminescence NO Analyzers® (NOA 280i, GE Analytical, Boulder, Colo., USA). Each test was conducted until a baseline NO measurement was achieved.

Nitric oxide recovery for the polymer film and the polymer nanofiber under physiological test conditions was also determined as described above in Example 3. Table 2 summarizes the results.

TABLE 2

| Polymer | NO loading mmol SNO/g polymer | NO release | | |
|---|---|---|---|---|
| | | Thermal mmol/g polymer | Polymer film mmol/g polymer | Nanofiber mmol/g polymer |
| S-nitrosated PLGH-cysteamine | 0.53 ± 0.01 | 0.461 ± 0.016 (% NO recovery: 87, equivalent to 3 7 mmol NO/g from 4.26 mmol NO donor/g) | 0.241 ± 0.004 (% NO recovery: 46, equivalent to 1.96 mmol NO/g from 4.26 mmol NO donor/g) | 0.28 ± 0.02 (% NO recovery: 52, equivalent to 2.22 mmol NO/g from 4.26 mmol NO donor/g) |
| S-nitrosated PLGH-cysteine | 0.17 ± 0.01 | 0.162 ± 0.010 (% NO recovery: 97, equivalent to 4.13 mmol NO/g from 4.26 mmol NO donor/g) | 0.155 ± 0.009 (% NO recovery: 93, equivalent to 3.96 mmol NO/g from 4.26 mmol NO donor/g) | 0.11 ± 0.01 (% NO recovery: 65, equivalent to 2.77 mmol NO/g from 4.26 mmol NO donor/g) |
| S-nitrosated PLGH-homocysteine | 0.17 ± 0.01 | 0.141 ± 0.010 (% NO recovery: 83, equivalent to 3.53 mmol NO/g from 4.26 mmol NO donor/g) | 0.033 ± 0.007 (% NO recovery: 20, equivalent to 0.85 mmol NO/g from 4.26 mmol NO donor/g) | 0.03 ± 0.01 (% NO recovery: 18, equivalent to 0.77 mmol NO/g from 4.26 mmol NO donor/g) |

The rate of nitric oxide recovery is based on the conditions employed to trigger the release. Under thermal test conditions, nitric oxide recovery of at least about 83% is achieved.

Example 7

Nitric Oxide Releasing Diazeniumdiolated PLGH-DETA

Figure 7:
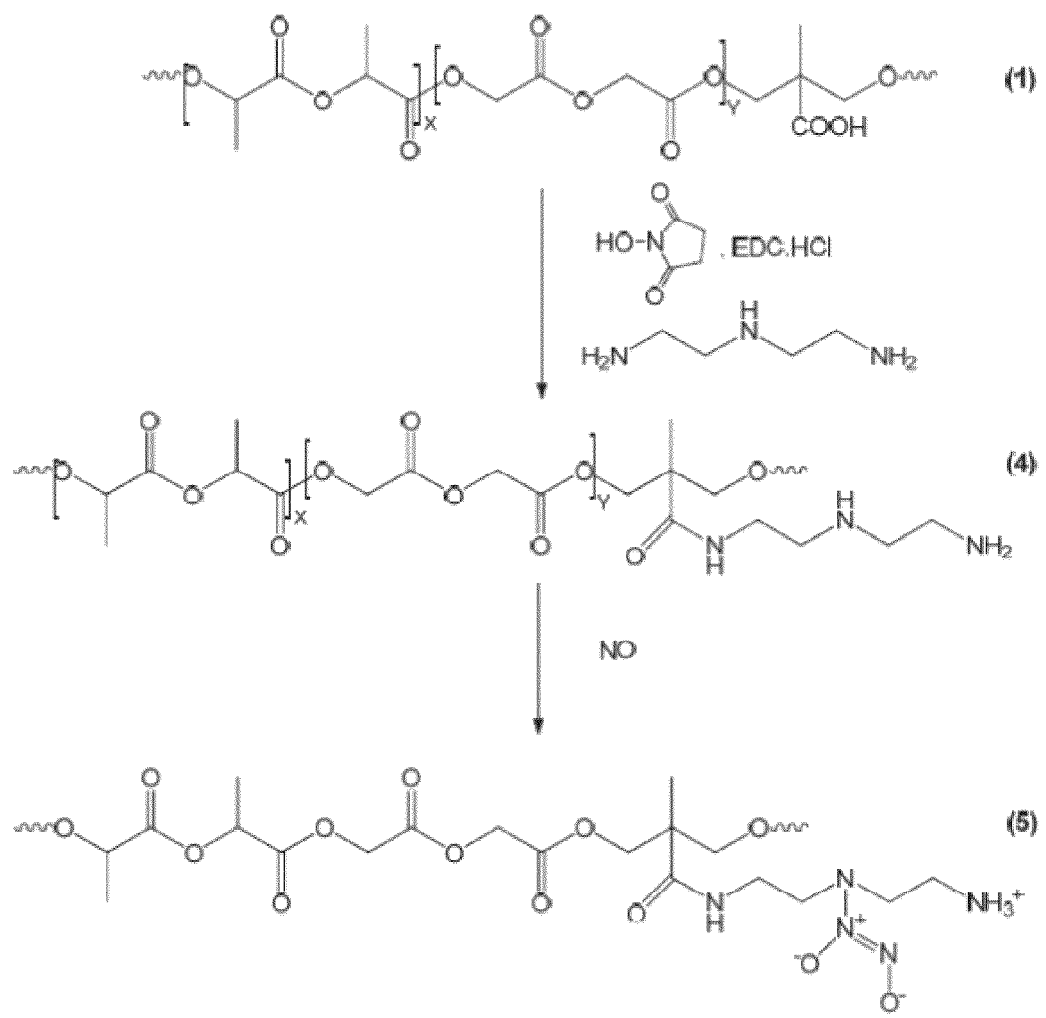
FIG. 7 illustrates a synthesis of NO releasing diazeniumdiolated PLGH-DETA.

FIG. 7 is a scheme for preparing a NO releasing diazeniumdiolated polymer by reacting diethylenetriamine (DETA) with NHS activated PLGH (1) followed by treating with NO under pressure.

Example 8

NO Releasing Polymeric Nanostructures

S-nitrosated PLGH derivatives (Example 1) were electrospun in a suitable solvent into nanofibers. These electrospun nanofibers were evaluated for NO releasing kinetics in Example 6.

DETA modified PLGH derivatives (Example 7) will be electrospun into nanofibers and will be loaded with NO under suitable pressure followed by evaluating their NO release kinetics.

Example 9

Modification of Dextran with NO Donor

Figure 8:
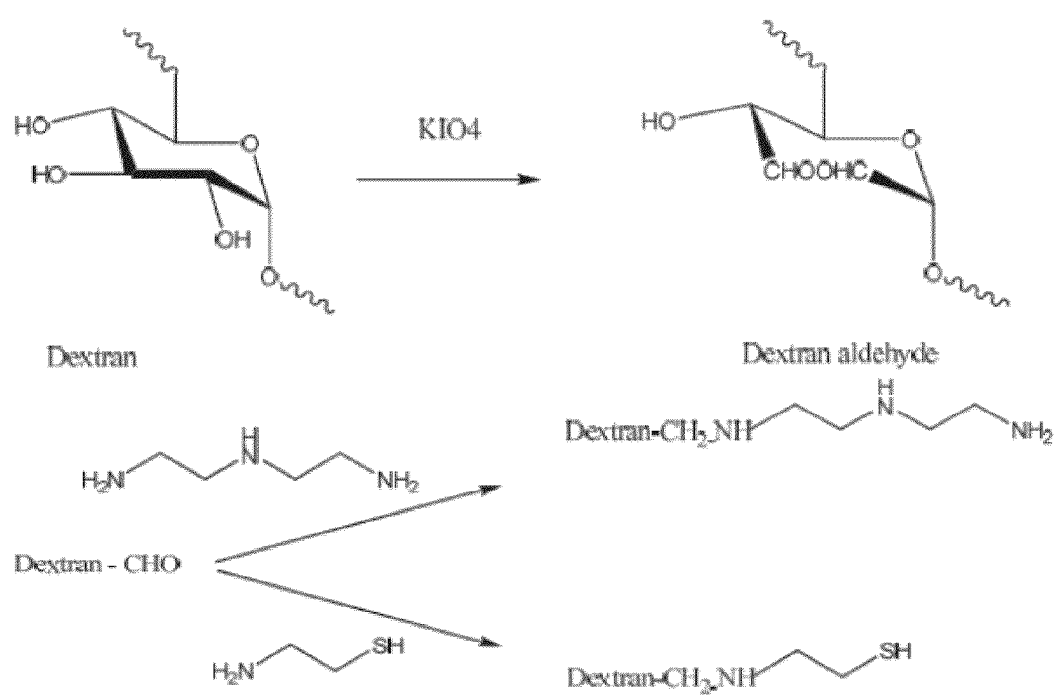
FIG. 8 illustrates dextran modifications using reductive amination.
Figure 9:
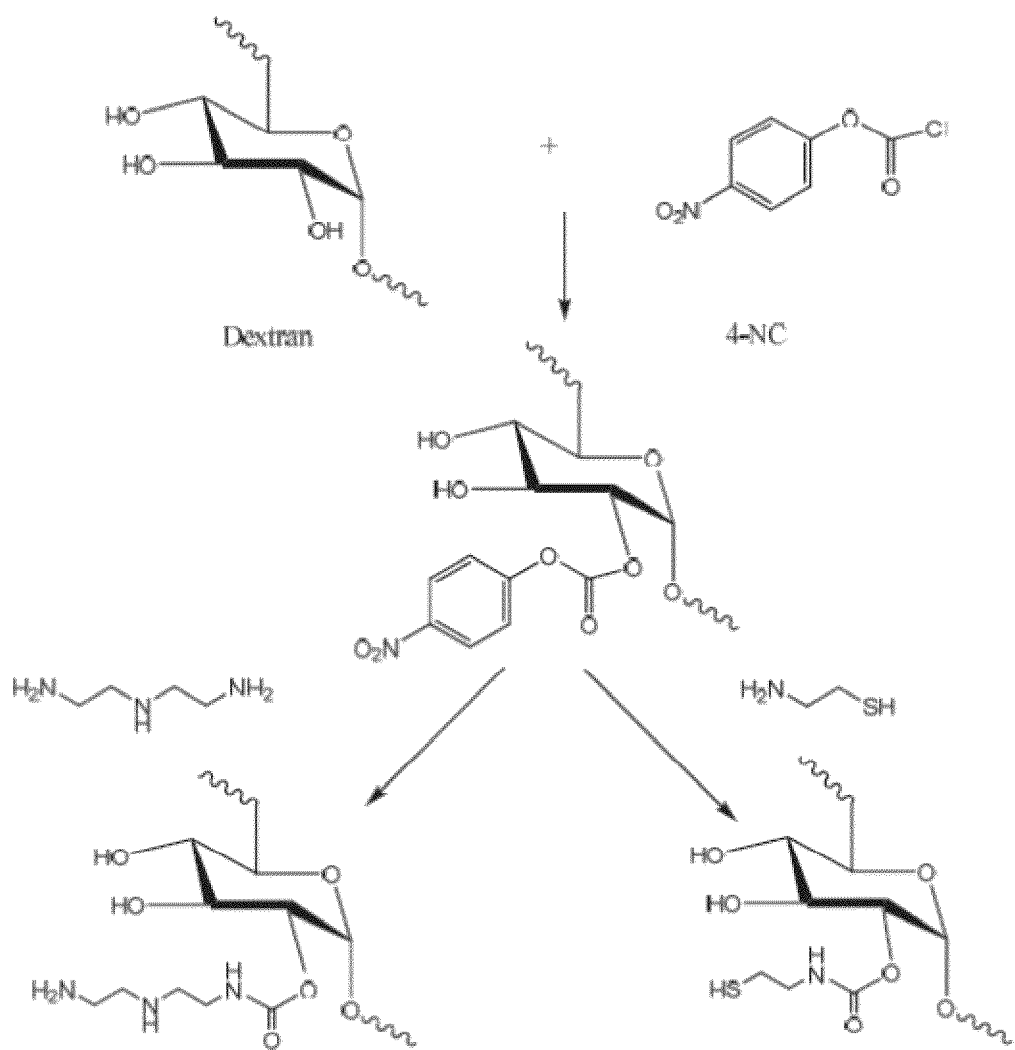
FIG. 9 illustrates dextran modifications using 4-nitrophenyl chloroformate activation.

Dextran modified with suitable NO donors can be prepared either by following reductive amination (FIG. 8) or through using 4-nitrophenyl chloroformate activation (FIG. 9). The modified dextran may be suitable for use as biomimetic nanoscaffolds for tissue engineering.

Example 10

NO Releasing S-Nitrosated Dextran Derivatives Through Reductive Amination

Figure 10:
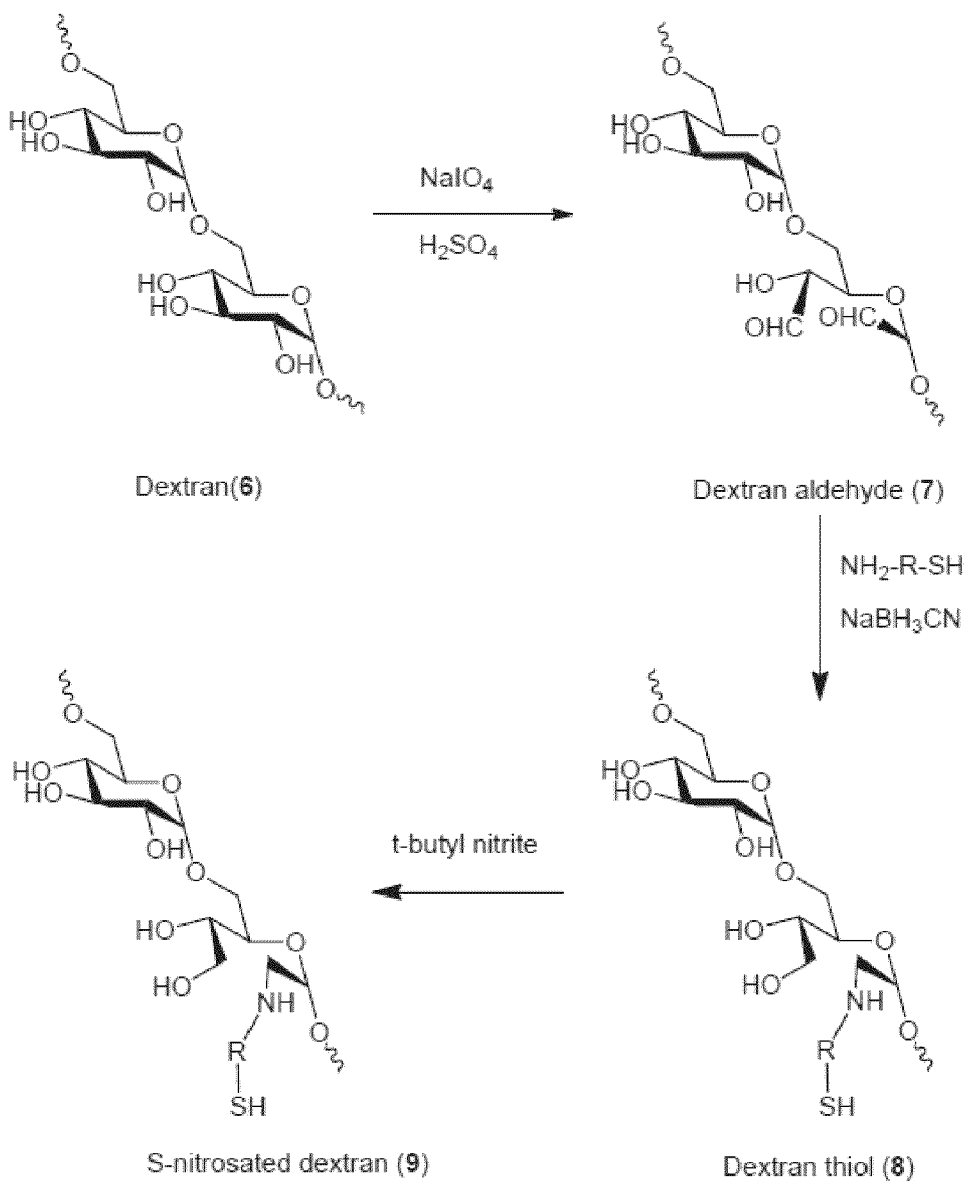
FIG. 10 illustrates a synthesis of a S-nitrosated dextran derivatives.

FIG. 10 is a scheme for preparing NO releasing S-nitrosated dextran derivatives through reductive amination.

S-Nitrosated Dextran-Cysteamine Through Reductive Amination (9a):

To a solution of 1 g dextran in 30 mL Millipore water, 0.8 g sodium periodate (3.73 mmol) was added followed by 0.3 g conc. sulfuric acid (3 mmol, 0.8 eq. of periodate). The reaction mixture was protected from direct exposure to light and stirred for 1.5 h at room temperature. Reaction was terminated by treating with 0.18 g ethylene glycol (2.84 mmol, 0.76 eq.) for half an hour and then neutralized with 0.2 M sodium acetate solution. The resulting mass was extensively dialysed against Millipore water using Spectra/Por® dialysis membrane (Spectrum Laboratories, CA) with a MW cut-off size of 2000 Da. Dialyzed reaction mass containing dextran aldehyde derivative (7) was cooled to 0° C. in an ice bath and 0.46 g cysteamine hydrochloride (1.05 molar eq. based on the periodate quantity) was added. The pH of the reaction mixture was adjusted to 8.5 by the addition of 1 M sodium hydroxide solution and stirred at 0° C. for one hour. Sodium cyanoborohydride (0.25 g, 1 eq.) was then added and the solution was stirred for further 2 h at the same temperature. The reaction mass was neutralized with 10% acetic acid and after an overnight dialysis with Millipore water, the dialyzed solution was stirred with 0.05 g dithioerythritol (DTE) for one hour at room temperature to reduce any disulfide formation. The solution was further extensively dialyzed and freeze dried to isolate the cysteamine modified dextran derivative (8a).

S-nitrosation of the thiol terminals was performed by suspending 100 mg of the dextran-cysteamine derivative (8a) in 8 mL anhydrous methanol (80 vol.) and stirred to get a uniform suspension. To this, 0.8 mL tert-butylnitrite, pre-treated with 10% w/v disodium ethylenediamine tetraacetate dehydrate (EDTA-disodium salt), was added and stirred for 24 h at room temperature under an $N_2$ atmosphere, protected from light. Excess tert-butylnitrite was removed by washing with anhydrous methanol (3×8 mL) and dried under vacuum to isolate the S-nitrosated dextran-cysteamine derivative (9a) as an orange coloured powder.

The extent of thiol incorporation onto the dextran backbone was quantified using Ellman's assay (Ellman, G. L. (1959). Tissue sulfhydryl groups. Archives of Biochemistry and Biophysics, 82(1), 70-77; Frost, M. C., & Meyerhoff, M. E. (2005). Synthesis, characterization, and controlled nitric oxide release from S-nitrosothiol-derivatized fumed silica polymer filler particles. Journal of Biomedical Materials Research Part A, 72A(4), 409-419.) using cysteine standards. The thiol content was determined to be 0.16 mmol SH/g. Nitric oxide release was determined as described in Example 11. The NO release was determined to be 0.085 mmol NO/g, which is equivalent to 53% NO release, based on SH.

S-Nitrosated Dextran-Cysteine Through Reductive Amination (9b):

Experiments were performed following the method given for 9a using 0.48 g cysteine (1.05 molar eq. based on the periodate quantity) and S-nitrosated following the same reaction parameters given for 8a.

The thiol content and NO release were determined as described above for S-nitrosated dextran-cysteamine through reductive amination (9a). The thiol content was 0.263 mmol SH/g, and the NO release was 0.139 mmol NO/g (53% NO release based on SH).

Example 11

NO Release from the S-Nitrosated Dextran Derivatives Through Reductive Amination NO release from S-nitrosated dextran-cysteamine (9a) and dextran-cysteine (9b) of Example 10 were measurements using chemiluminescence NO analyzer. The polymer materials were tested in phosphate buffer saline (PBS, 10 mM phosphate, pH 7.4) at 37° C. The release profile from S-nitrosated dextran-cysteamine (9a) and dextran-cysteine (9b) are represented in FIGS. 11 and 12 respectively.

Figure 11:
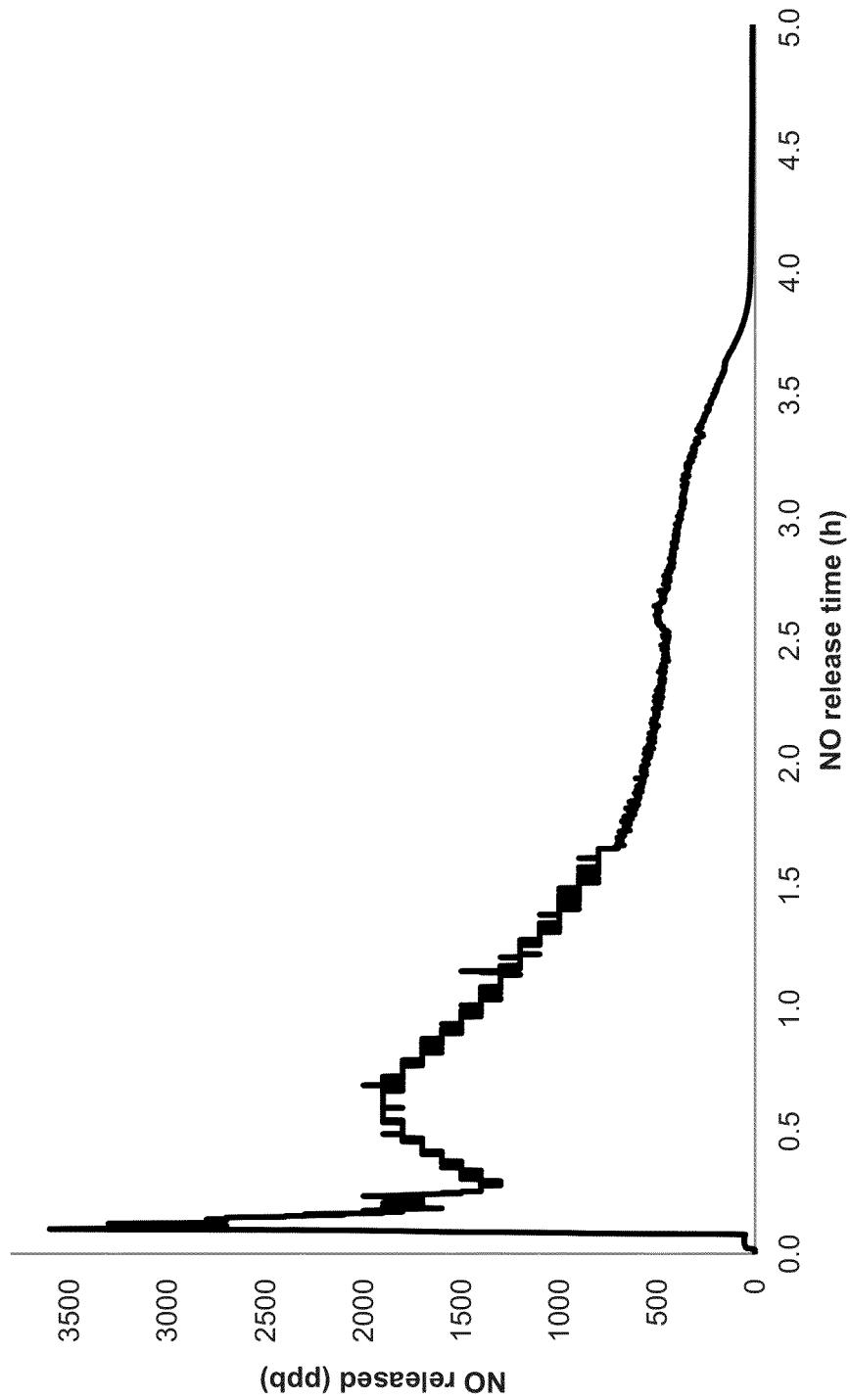
FIG. 11 is a graph illustrating a NO release profile of S-nitrosated dextran-cysteamine derivative (9a) in phosphate buffer saline (PBS, 10 mM phosphate, pH 7.4) at 37° C.
Figure 12:
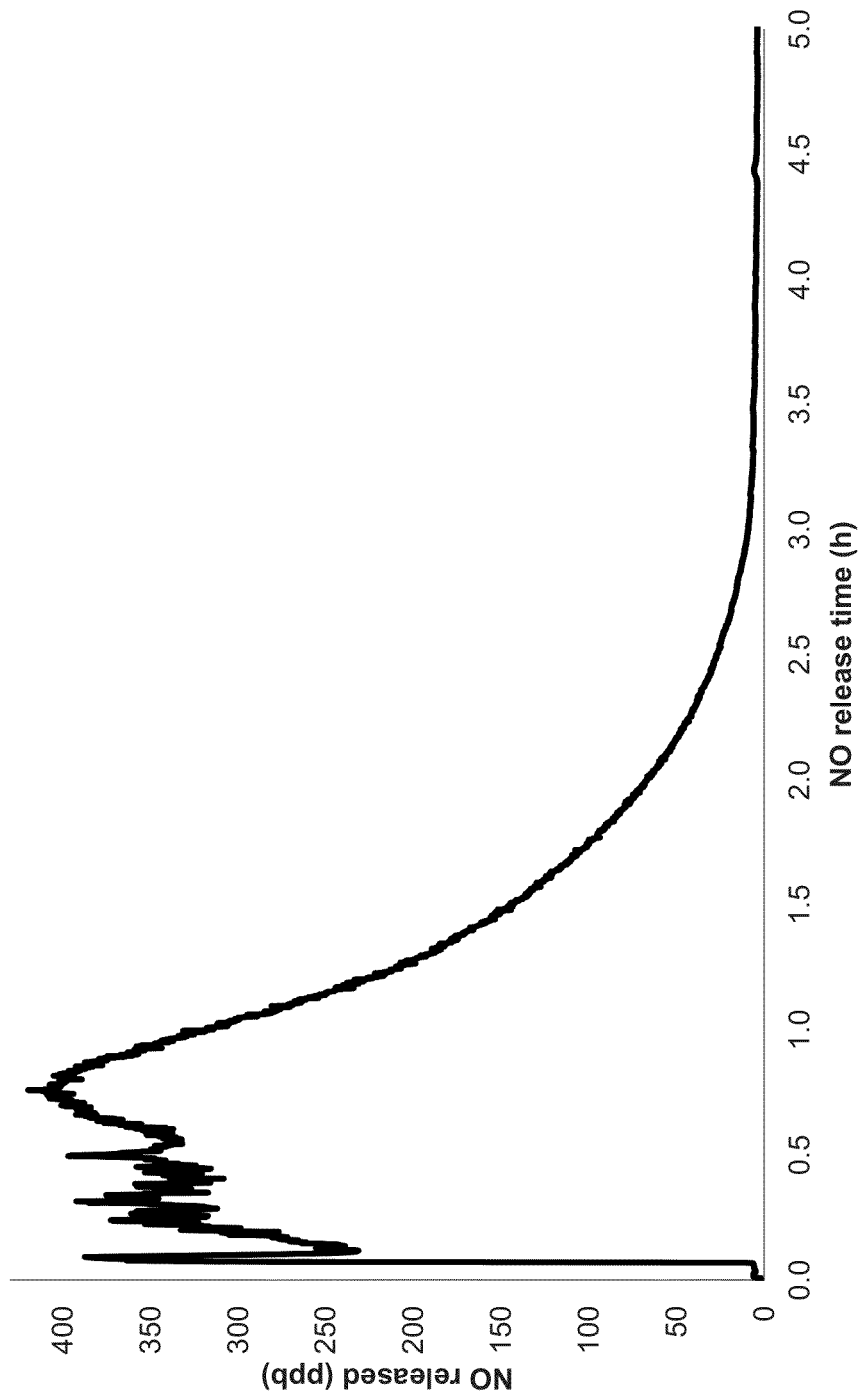
FIG. 12 is a graph illustrating a NO release profile of S-nitrosated dextran-cysteine derivative (9b) in phosphate buffer saline (PBS, 10 mM phosphate, pH 7.4) at 37° C.

FIGS. 11 and 12 illustrate the high NO release rates from S-nitrosated dextran-cysteamine (9a) and dextran-cysteine (9b). The NO release amounts are sufficient to modulate cell responses. These materials are also degradable using enzymes.

Example 12

NO Releasing S-Nitrosated Dextran Derivatives Through Carboxymethylation

Figure 13:
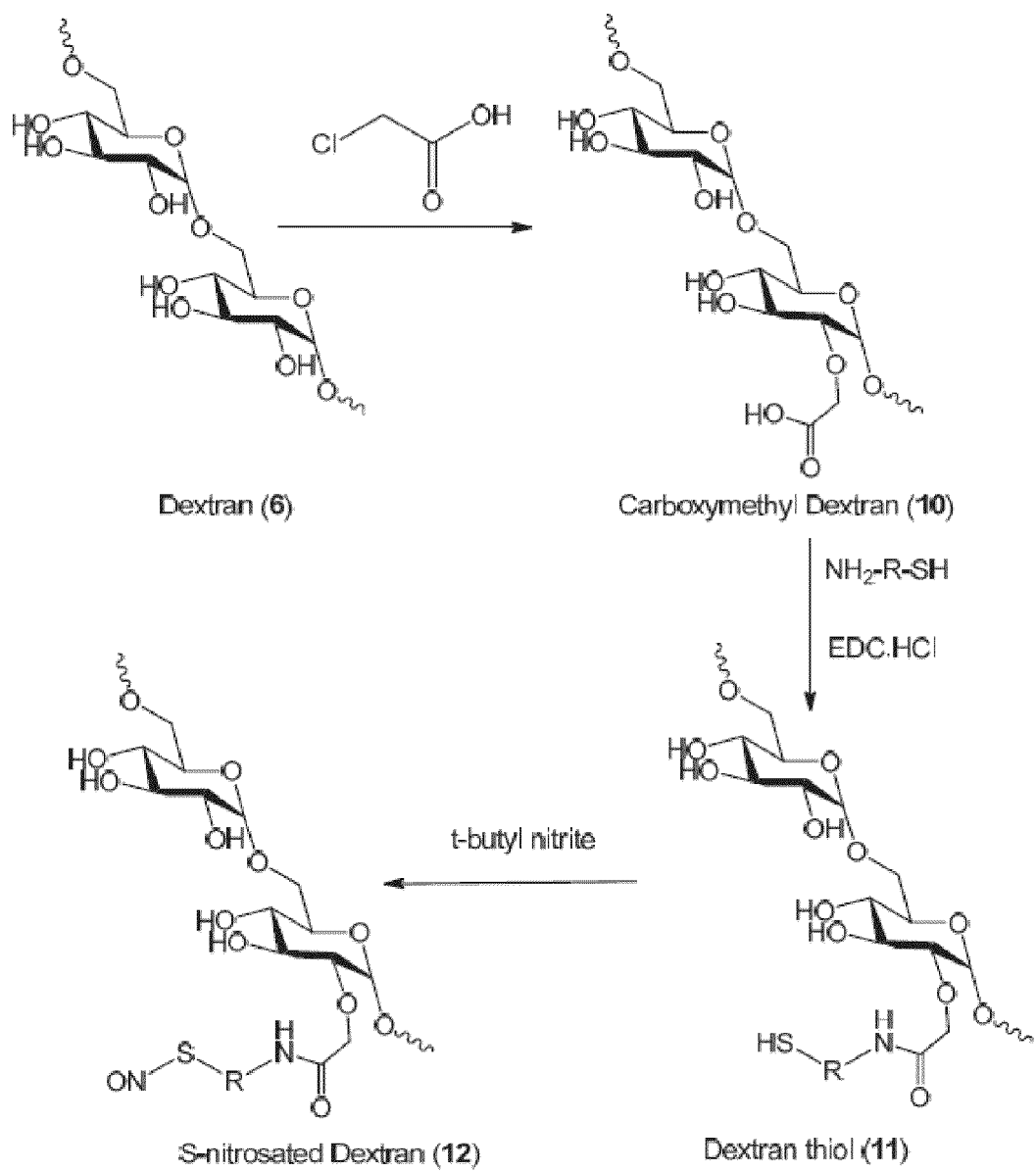
FIG. 13 illustrates a synthesis of a S-nitrosated dextran derivatives through carboxymethylation of dextran.

FIG. 13 is a scheme for preparing NO releasing S-nitrosated dextran derivatives through carboxymethylation.

Preparation of Carboxymethyl Dextran Derivative (10):

CM-dextran derivative was prepared following a modified procedure reported previously (Langmuir, 26, 7299 (2010)). Dextran (5 g) and sodium hydroxide (5 g, 125 mmol) were mixed together in 125 mL 80% 2-propanol solution and stirred at 60° C. to get a clear solution. A solution of 5.62 g chloroacetic acid (59 mmol, 0.47 eq. of NaOH) in 40 mL 80% IPA solution was prepared separately and slowly charged to the reaction mass using a pressure equilibrium addition funnel over a period of half an hour. After maintaining at 60° C. for five hour, the reaction mass was cooled to room temperature and adjusted the pH to 5 by the addition of glacial acetic acid. The reaction mass was maintained at this pH for one hour with occasional addition of acetic acid and slowly quenched into methanol (1 L) and stirred for one hour to ensure the complete precipitation of the product. The crude product was isolated by filtration, washed with methanol and dried under vacuum. Redissolved the product in 25 mL Millipore water and adjusted the pH to 5 by the addition of glacial acetic acid (if needed) and dialyzed against Millipore water using a MWCO membrane (2000 Da) for one week with multiple changes per day. Finally the dialysis product was freeze-dried over 3 days to isolate the product as a white fluffy powder.

Dextran-Cysteamine Derivative (11a):

Carboxyl groups of the CM-dextran derivative (1 g, equivalent to 1.5 mmol carboxyl content) was pre-activated by reacting with NHS (1.5 g, 12.75 mmol, 8.5 molar eq.) and EDC.HCl (2.5 g, 12.75 mol, 8.5 molar eq.) in Millipore water (25 mL) for 30 minutes at 25° C. To this, a solution of 3.5 g cysteamine hydrochloride (30 mmol, 20 molar eq.) was charged. Adjusted the pH to 5 by the addition of 0.1 M HCl (if needed) and stirred at 25° C. for 5 hour. Dialyzed the mass against Millipore water (pH adjusted to 5 using 0.1 M HCl) using a MWCO membrane (2000 Da) for two weeks with multiple changes per day and protected from direct exposure to light. Finally, the product was isolated as a white fluffy powder by freeze-drying the dialyzed mass for three days.

Dextran-Cysteine Derivative (11b):

Cysteine modified dextran derivative (11b) was prepared following the method given for 11a using 3.7 g cysteine (30 mmol, 20 molar eq.).

S-Nitrosated Dextran-Cysteamine (12a):

100 mg dextran-cysteamine (11a) was mixed with 4 mL anhydrous methanol and stirred to get a uniform suspension. 0.4 mL t-butyl nitrite was charged and stirred the mass at 20° C. for 24 hour under $N_2$, protected from direct exposure to light. S-nitrosated dextran derivative was isolated by concentrating the product under vacuum, and stored under $N_2$ at −16° C.

The thiol content was determined as described in Example 10 to be 0.21 mmol SH/g.

S-Nitrosated Dextran-Cysteine (12b):

The dextran-cysteine derivative (11b) was nitrosated to yield 12b following the method given for 12a.

The thiol incorporation of the dextran-cysteine derivative (11b) was calculated by integrating the NMR intensities of the thiol protons and those of dextran. The nitric oxide loading was determined to be 0.1412 mmol NO/g polymer, which is 50% thiol conversion based on SH content, 80% thiol conversion based on SNO content.

The thiol content was determined as described above in Example 10 and the nitric oxide release was determined according to Example 13. The thiol content was 0.281 mmol SH/g and the nitric oxide content was 0.1772 mmol SNO/g, which is a 63% thiol conversion. The nitric oxide release was 0.141 mmol NO/g, which is a 50% NO release based on SH and an 80% NO release based on SNO.

Example 13

NO Release from the NO Releasing S-Nitrosated Dextran Derivatives Through Carboxymethylation NO release was measured using chemiluminescence NO analyzer under physiological conditions (in phosphate buffer saline (PBS, 10 mM phosphate, pH 7.4) at 37° C.). The NO release profile from S-nitrosated dextran-cysteine (12b) of Example 12 is given in FIG. 14.

Figure 14:
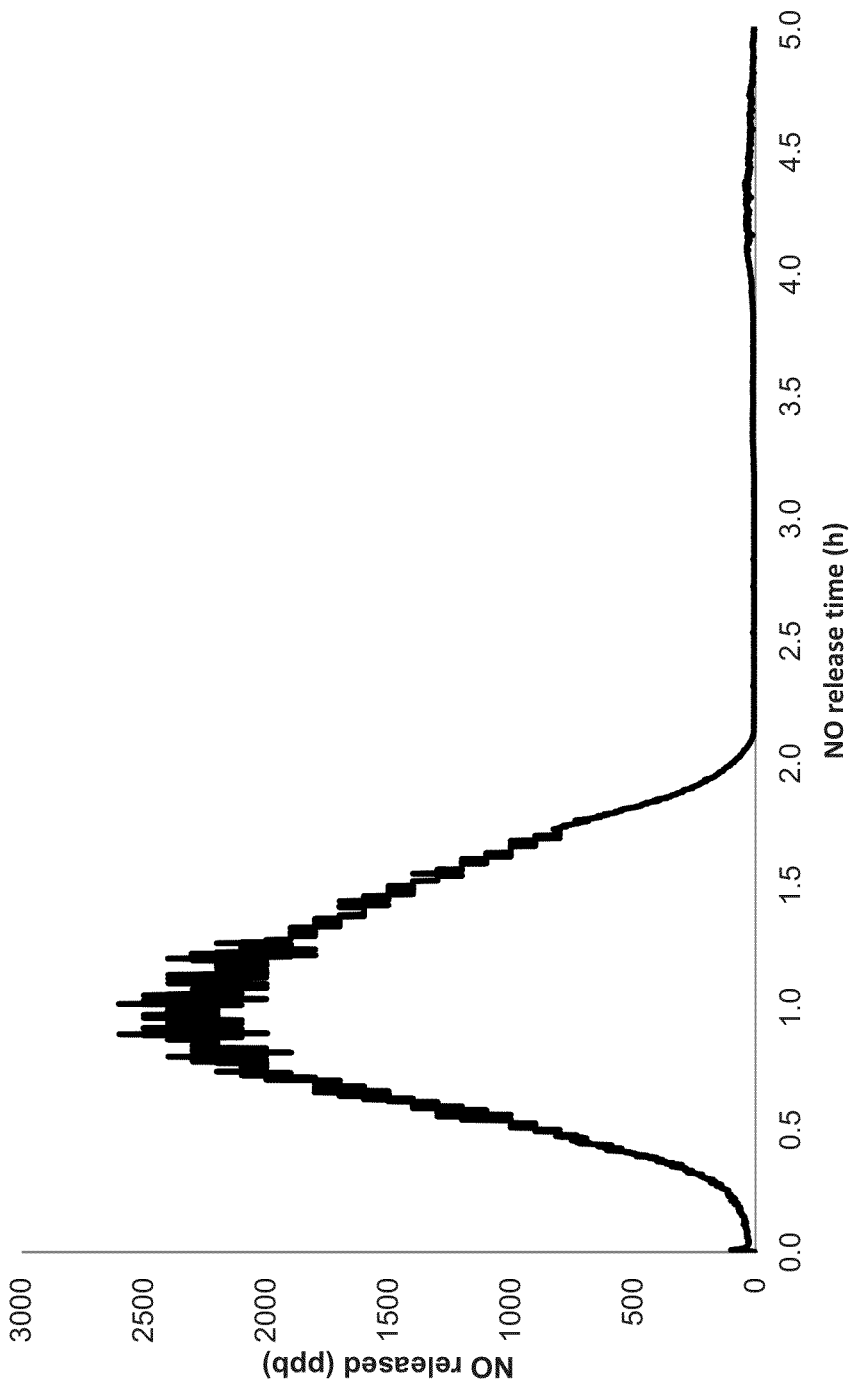
FIG. 14 is a graph illustrating a NO release profile of S-nitrosated dextran-cysteine (12b) under physiological conditions.

FIG. 14 demonstrates the high NO release rates from S-nitrosated dextran-cysteine (12b). FIG. 14 also illustrates sufficient NO release amounts to modulate cell responses in a similar manner to examples 11-12. The synthesis of Example 13 provides the advantage of selectively nitrosating only the thiol moiety for this class of polysaccharide materials, enabling the ability to better trigger and/or extend the NO release capabilities when processing because the mechanisms of release are known. These materials are also degradable using enzymes.

Example 14

NO Releasing Chitosan Derivative

Figure 15:
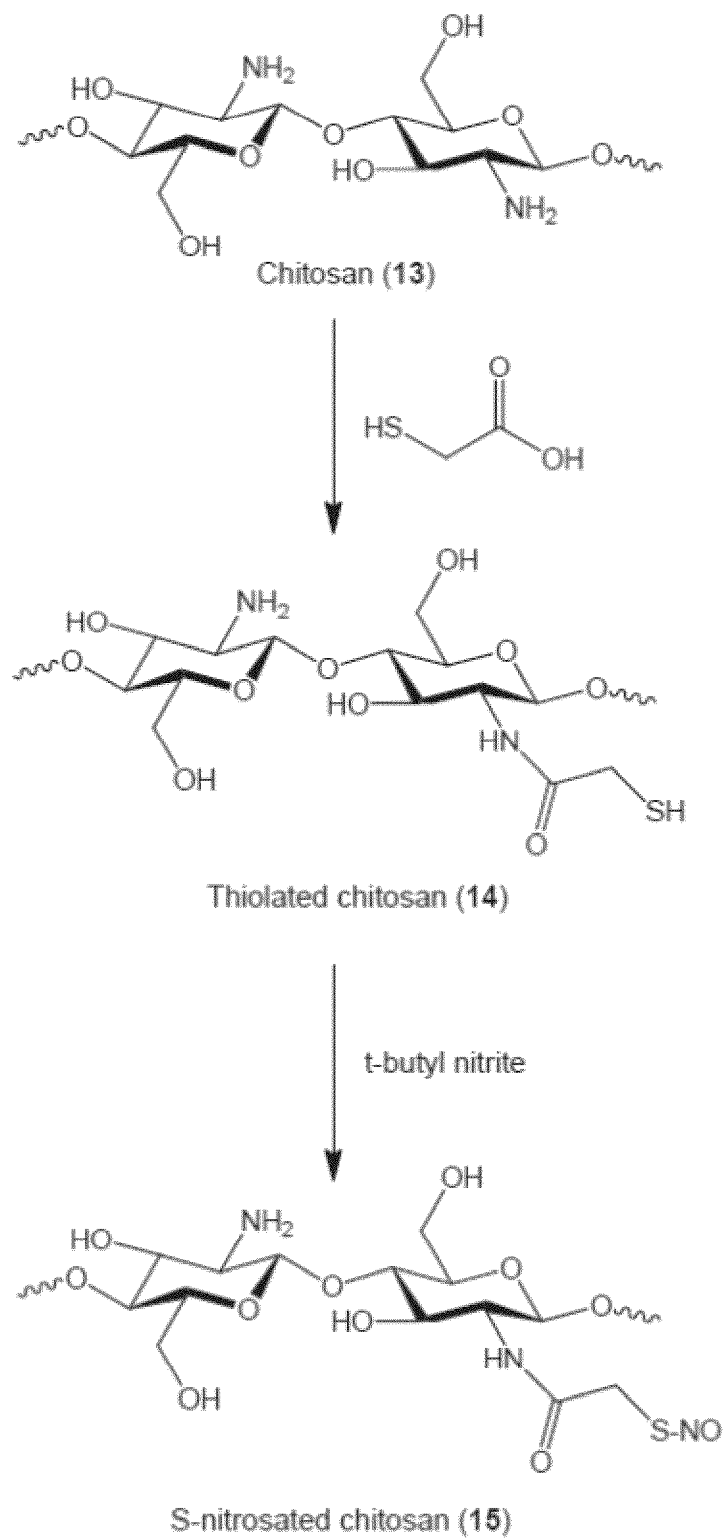
FIG. 15 illustrates a synthesis of a S-nitrosated chitosan derivative.

FIG. 15 is a scheme for preparing an NO releasing chitosan derivative.

Thiolated Chitosan Derivative (14):

To a solution of 0.5 g chitosan (80% deacetylated) in 100 mL 1% acetic acid solution (in Millipore water), 1.9 g EDC.HCl (10 mmol) and 1 g thioglycolic acid (10.6 mmol) was charged and stirred overnight at room temperature protected from light. The reaction mixture was dialyzed against Millipore water (pH adjusted to 5 using 0.1 M HCl) using a MWCO membrane (2000 Da) for two days against Millipore water with multiple changes per day. The dialyzed mass was then treated with 0.2 g DTT at room temperature for 1 hour and then re-dialyzed for one week. Finally, the thiolated chitosan derivative (14) was isolated by freeze-drying for three days.

S-Nitrosated Chitosan Derivative (15):

100 mg chitosan-thiol derivative (14) was mixed with 4 mL anhydrous methanol and stirred to get a uniform suspension. 0.4 mL t-butyl nitrite was charged and stirred the mass at 20° C. for 24 hour under $N_2$, protected from direct exposure to light. S-nitrosated chitosan derivative was isolated by concentrating the product under vacuum, and stored under $N_2$ at −16° C.

Example 15

NO Release from the NO Releasing Chitosan Derivative

NO release was measured using a chemiluminescence NO analyzer under physiological conditions. The NO release profile from S-nitrosated chitosan derivative is given in FIG. 16. The NO release was determined to be 0.14 mmol NO/g.

Figure 16:
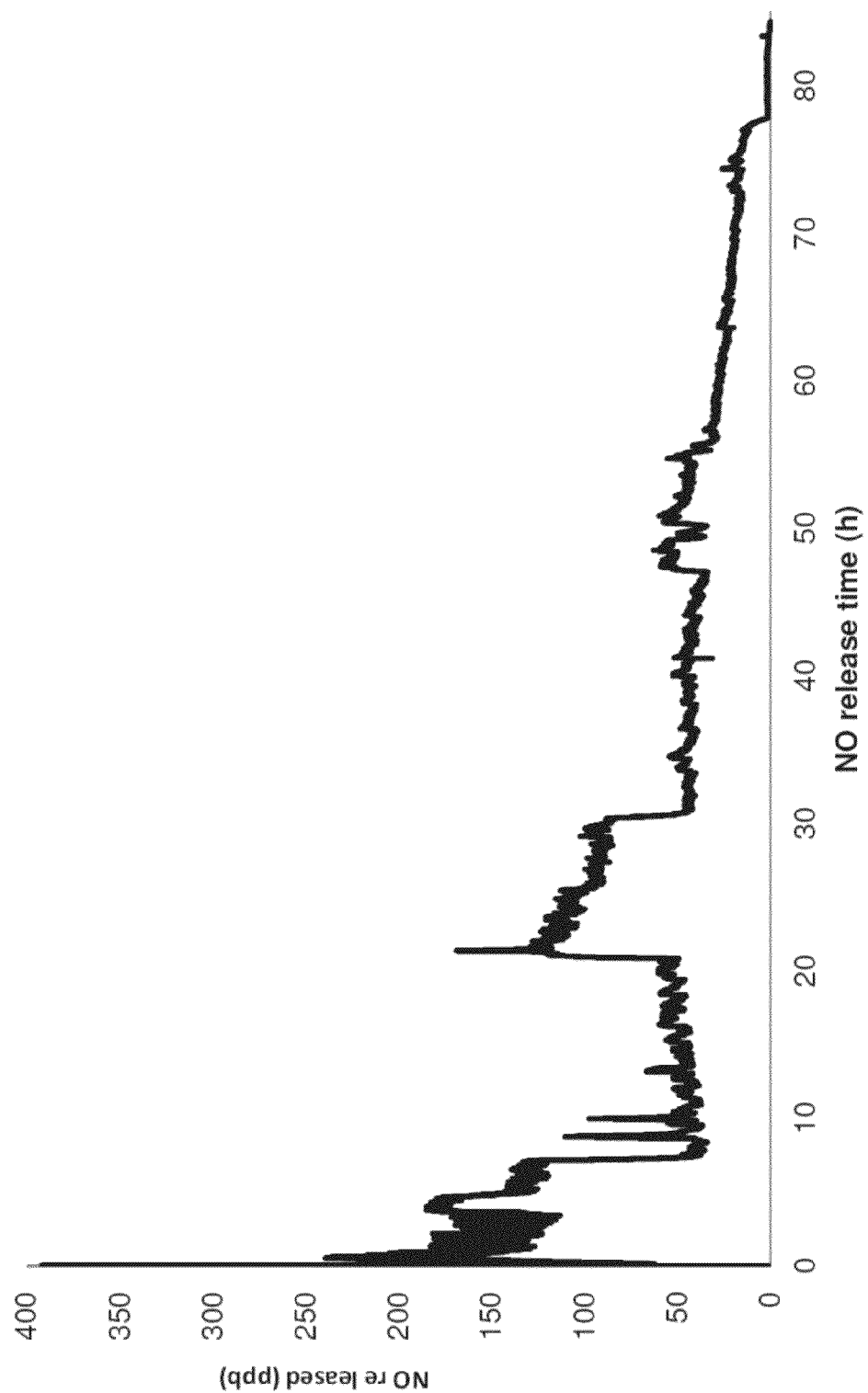
FIG. 16 is a graph illustrating a NO release profile from S-nitrosated chitosan derivative in phosphate buffer saline (PBS, 10 mM phosphate, pH 7.4) at 37° C.

FIG. 16 illustrates that the saccharide based material of Example 15 has extended NO release compared to its dextran counterpart (i.e., examples 9-14)

Example 16

PLGH-Dextran Conjugate

Figure 17:
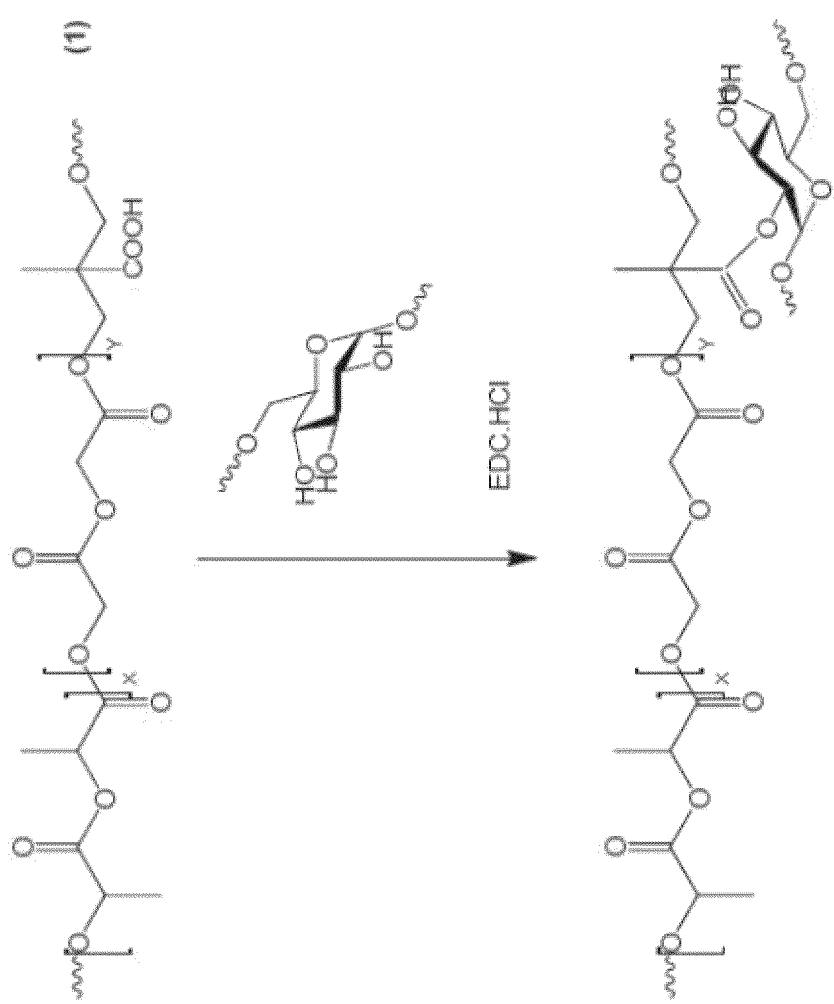
FIG. 17 illustrates a synthesis of a PLGH-dextran conjugate.

Dextran modified block polymers can be prepared by chain extension by reacting PLGH (Example 1) or similar carboxyl functionalized polymer with functionalized dextran having NO donors. One such strategy is illustrated in FIG. 17, which involves grafting dextran onto our early reported PLGH using the well-known carbodiimide mediated esterification reaction. Incorporating dextran covalently onto the polymer backbone results in crosslinking of the polymer and provides sufficient physical strength to the polymer for tissue engineering applications. In addition, the degree of substitution (DS) on the dextran groups can be conveniently varied to optimize NO loading and release to the final requirement. Moreover, a favorable degradation profile is also anticipated by the influence of dextran hydroxyl groups on the nearby ester linkages. Because of the presence of multi-block polymeric segments with different hydrolysable characteristics, the resulting polymer derivative will be anticipated to provide a unique and multifaceted degradation pathway to complement their compatibility to use for various biomedical applications.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A method of forming a nitric oxide releasing biocompatible polymer for modulating biological response, the method comprising:
   a. activating carboxyl groups of a biocompatible polymer in a non-aqueous solution by reaction with N-hydroxysuccinimide; and
   b. converting thiol residues on the biocompatible polymer to S-nitrosated residues under non-aqueous conditions, wherein at least about 40% of thiol residues are converted to S-nitrosated residues.

2. The method of claim 1, wherein the nitric oxide releasing biocompatible polymer comprises at least about 0.1 mmol of nitric oxide per 1 gram of the nitric oxide releasing biocompatible polymer.

3. The method of claim 1, wherein the nitric oxide releasing biocompatible polymer comprises at least about 0.4 mmol of nitric oxide per 1 gram of the nitric oxide releasing biocompatible polymer.

4. The method of claim 1, wherein the method further comprises forming the biocompatible polymer into a nanofiber after converting the thiol residues.

5. The method of claim 1, wherein the S-nitrosated residues are residues from at least one member selected from the group consisting of: cysteamine, cysteine, and homocysteine.

6. The method of claim 1, wherein the biocompatible polymer comprises a member selected from the group consisting of: polylactide, polyglycolide, poly(lactide-co-glycolide), poly(ε-caprolactone), chitosan and dextran.

7. The method of claim 1, wherein the biocompatible polymer comprises poly(lactide-co-glycolide).

8. The method of claim 7, wherein the S-nitrosated residues include residues from cysteamine.

9. The method of claim 7, wherein the S-nitrosated residues include residues from cysteine.

10. The method of claim 7, wherein the S-nitrosated residues include residues from homocysteine.

11. The method of claim 1, wherein the biocompatible polymer comprises poly(lactic-co-glycolic-co-hydroxymethyl propionic acid).

12. The method of claim 1, wherein the biocompatible polymer comprises dextran.

13. The method of claim 12, wherein the S-nitrosated residues include residues from cysteine.

14. The method of claim 12, wherein the S-nitrosated residues include residues from cysteamine.

15. The method of claim 1, wherein the biocompatible polymer comprises chitosan.

16. The method of claim 1, wherein the biocompatible polymer comprises dextran and poly(lactic-co-glycolic-co-hydroxymethyl propionic acid).

* * * * *